(12) United States Patent
He et al.

(10) Patent No.: US 7,684,858 B2
(45) Date of Patent: Mar. 23, 2010

(54) METHODS AND SYSTEMS FOR PLACING AN IMPLANTED STIMULATOR FOR STIMULATING TISSUE

(75) Inventors: Tom Xiaohai He, Simi Valley, CA (US); Todd K. Whitehurst, Santa Clarita, CA (US); Alfred E. Mann, Beverly Hills, CA (US); Peter K. Johnson, Newhall, CA (US)

(73) Assignee: Boston Scientific Neuromodulation Corporation, Valenica, CA (US)

( * ) Notice: Subject to any disclaimer, the term of this patent is extended or adjusted under 35 U.S.C. 154(b) by 1218 days.

(21) Appl. No.: 11/232,540

(22) Filed: Sep. 21, 2005

(65) Prior Publication Data
US 2007/0066997 A1 Mar. 22, 2007

(51) Int. Cl.
*A61N 1/36* (2006.01)
(52) U.S. Cl. .......................................... 607/2
(58) Field of Classification Search .............. 607/3, 607/2, 61
See application file for complete search history.

(56) References Cited

U.S. PATENT DOCUMENTS

| | | | |
|---|---|---|---|
| 3,760,984 A | 9/1973 | Theeuwes | |
| 3,845,770 A | 11/1974 | Theeuwes et al. | |
| 3,916,899 A | 11/1975 | Theeuwes et al. | |
| 3,923,426 A | 12/1975 | Theeuwes et al. | |
| 3,987,790 A | 10/1976 | Eckenhoff et al. | |
| 3,995,631 A | 12/1976 | Higuchi et al. | |
| 4,016,880 A | 4/1977 | Theeuwes et al. | |
| 4,036,228 A | 7/1977 | Theeuwes | |
| 4,111,202 A | 9/1978 | Theeuwes | |
| 4,111,203 A | 9/1978 | Theeuwes | |
| 4,203,440 A | 5/1980 | Theeuwes | |
| 4,203,442 A | 5/1980 | Michaels | |
| 4,210,139 A | 7/1980 | Higuchi | |
| 4,327,725 A | 5/1982 | Cortese et al. | |
| 4,360,019 A | 11/1982 | Porter et al. | |
| 4,487,603 A | 12/1984 | Harris | |
| 4,515,167 A * | 5/1985 | Hochman | 600/549 |

(Continued)

FOREIGN PATENT DOCUMENTS

WO WO 98/02209 1/1998

OTHER PUBLICATIONS

Medtronic, "New Diagnostic Tool—Reveal? Insertable Loop Recorder" http://www.medtronic.com/reveal/new.html.

*Primary Examiner*—Carl H Layno
*Assistant Examiner*—Brian T Gedeon
(74) *Attorney, Agent, or Firm*—Vista IP Law Group LLP

(57) ABSTRACT

Systems for providing stimulation with an implantable system control unit and for optimally positioning that system control unit include a system control unit configured to provide a stimulus to a patient with a member attached to the system control unit for pulling the system control unit into position within the patient. Methods of optimally positioning the implantable system control unit within a patient such that the system control unit is proximal to target tissue that is to be stimulated by the system control unit include threading a member through a patient's body using a needle, the member passing proximal to the target tissue and being attached to the system control unit, and pulling the system control unit into place with the member.

27 Claims, 12 Drawing Sheets

U.S. PATENT DOCUMENTS

| | | |
|---|---|---|
| 4,627,850 A | 12/1986 | Deters et al. |
| 4,692,147 A | 9/1987 | Duggan |
| 4,725,852 A | 2/1988 | Gamblin et al. |
| 4,865,845 A | 9/1989 | Eckenhoff et al. |
| 5,057,318 A | 10/1991 | Magruder et al. |
| 5,059,423 A | 10/1991 | Magruder et al. |
| 5,112,614 A | 5/1992 | Magruder et al. |
| 5,137,727 A | 8/1992 | Eckenhoff |
| 5,193,539 A | 3/1993 | Schulman et al. |
| 5,193,540 A | 3/1993 | Schulman et al. |
| 5,234,692 A | 8/1993 | Magruder et al. |
| 5,234,693 A | 8/1993 | Magruder et al. |
| 5,312,439 A | 5/1994 | Loeb |
| 5,405,367 A | 4/1995 | Schulman et al. |
| 5,728,396 A | 3/1998 | Peery et al. |
| 5,871,515 A * | 2/1999 | Wiklund et al. ............... 607/36 |
| 6,024,704 A | 2/2000 | Meador et al. |
| 6,051,017 A | 4/2000 | Loeb et al. |
| 6,061,596 A | 5/2000 | Richmond et al. |
| 6,164,284 A | 12/2000 | Schulman et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,214,032 B1 | 4/2001 | Loeb et al. |
| 6,234,973 B1 | 5/2001 | Meador et al. |
| 6,315,721 B2 | 11/2001 | Schulman et al. |
| 6,368,315 B1 | 4/2002 | Gillis et al. |
| 6,782,292 B2 * | 8/2004 | Whitehurst ................... 607/45 |
| 6,829,508 B2 * | 12/2004 | Schulman et al. ............ 607/116 |
| 7,444,180 B2 * | 10/2008 | Kuzma et al. ................... 607/2 |
| 2004/0220632 A1 | 11/2004 | Burnes |
| 2006/0184222 A1 * | 8/2006 | Camps et al. ................ 607/129 |

* cited by examiner

METHODS AND SYSTEMS FOR PLACING AN IMPLANTED STIMULATOR FOR STIMULATING TISSUE

BACKGROUND

A wide variety of medical conditions and disorders have been successfully treated using an implanted stimulator. Such a stimulator will typically stimulate internal tissue, such as a nerve, by emitting an electrical stimulation current according to programmed stimulation parameters.

One class of such implantable stimulators, also known as BION® devices (where BION® is a registered trademark of Advanced Bionics Corporation, of Valencia, Calif.), are typically characterized by a small, cylindrical housing that contains electronic circuitry that produces the desired electric stimulation current between spaced electrodes. These stimulators, also referred to as microstimulators, are implanted proximate to the target tissue so that the stimulation current produced by the electrodes stimulates the target tissue to reduce symptoms or otherwise provide therapy for a wide variety of conditions and disorders.

For example, urinary urge incontinence may be treated by stimulating the nerve fibers proximal to the pudendal nerves of the pelvic floor; erectile or other sexual dysfunctions may be treated by providing stimulation to the cavernous nerve(s). Other disorders, e.g., neurological disorders caused by injury or stroke, may be treated by providing stimulation to other appropriate nerve(s).

In U.S. Pat. No. 5,312,439, entitled Implantable Device Having an Electrolytic Storage Electrode, an implantable device for tissue stimulation is described. The '439 patent is incorporated herein by reference.

Another microstimulator known in the art is described in U.S. Pat. No. 5,193,539, "implantable Microstimulator", which patent is also incorporated herein by reference. The '539 patent describes a microstimulator in which power and information for operating the microstimulator is received through a modulated, alternating magnetic field in which a coil is adapted to function as the secondary winding of a transformer. The induction coil receives energy from outside the patient's body and a capacitor is used to store electrical energy which is released to the microstimulator's exposed electrodes under the control of electronic control circuitry.

In U.S. Pat. Nos. 5,193,540 and 5,405,367, which patents are incorporated herein by reference, a structure and method of manufacture of an implantable microstimulator is disclosed. The microstimulator has a structure which is manufactured to be substantially encapsulated within a hermetically-sealed housing inert to body fluids, and of a size and shape capable of implantation in a living body, with appropriate surgical tools. Within the microstimulator, an induction coil receives energy or data from outside the patient's body.

In yet another example, U.S. Pat. No. 6,185,452, which patent is likewise incorporated herein by reference, there is disclosed a device configured for implantation beneath a patient's skin for the purpose of nerve or muscle stimulation and/or parameter monitoring and/or data communication. Such a device contains a power source for powering the internal electronic circuitry. Such power supply is a battery that may be externally charged each day. Similar battery specifications are found in U.S. Pat. No. 6,315,721, which patent is additionally incorporated herein by reference.

Other microstimulator systems prevent and/or treat various disorders associated with prolonged inactivity, confinement or immobilization of one or more muscles. Such microstimulators are taught, e.g., in U.S. Pat. Nos. 6,061,596 ("Method for Conditioning Pelvis Musculature Using an Implanted Microstimulator"); 6,051,017 ("Implantable Microstimulator and Systems Employing the Same"); U.S. Pat. No. 6,175, 764 ("Implantable Microstimulator System for Producing Repeatable Patterns of Electrical Stimulation"); U.S. Pat. No. 6,181,965 ("Implantable Microstimulator System for Prevention of Disorders"); U.S. Pat. No. 6,185,455 ("Methods of Reducing the Incidence of Medical Complications Using Implantable Microstimulators"); and U.S. Pat. No. 6,214,032 ("System for Implanting a Microstimulator"). The applications described in these additional patents, including the power charging techniques, may also be used with the present invention. The '596, '017, '764, '965, '455, and '032 patents are incorporated herein by reference.

As will be readily appreciated, a key part of patient treatment using an implanted stimulator is the proper placement of the stimulator or stimulation electrodes proximate to the target tissue to be stimulated. If the stimulator or stimulation electrodes are optimally placed near the target tissue, stimulation can be affected over a wide range of parameters with optimally minimal power consumption.

To the contrary, if the stimulator or stimulation electrodes are not optimally placed near the target tissue, it becomes increasingly difficult to provide effective stimulation. Additional power may be consumed in attempts to provide effective stimulation, and, at some point, the stimulating current may become uncomfortable to the patient if the stimulation current is increased to compensate for poor placement of the stimulator or stimulation electrodes.

SUMMARY

Systems for providing stimulation with an implantable system control unit and for optimally positioning that system control unit include a system control unit configured to provide a stimulus to a patient with a member attached to the system control unit for pulling the system control unit into position within the patient. Methods of optimally positioning the implantable system control unit within a patient such that the system control unit is proximal to target tissue that is to be stimulated by the system control unit include threading a member through a patient's body, the member passing proximal to the target tissue and being attached to the system control unit, and pulling the system control unit into place with the member.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Methods and systems for positioning an implanted stimulator for treating many different types of medical, psychiatric, and neurological conditions and/or disorders are described herein. As will be described in detail below, a stimulator or system control unit (SCU) is implanted within a patient and positioned for optimal effect using floss strings attached to one or both ends of the SCU body.

As used herein and in the appended claims, the term "system control unit" or "SCU" will be used broadly to refer to any type of device that is implanted to deliver a stimulus to a patient. An SCU may be, or incorporate, but is not limited to, a stimulator, microstimulator, neurostimulator, neuromodulator, implantable pulse generator and the like. In some examples, the SCU includes a microstimulator that electrically stimulates a target nerve or other tissue. In some cases, the microstimulator is coupled directly to the target tissue. In some alternative embodiments, the SCU may include an implantable pulse generator (IPG) coupled to a number of electrodes that are, in turn, coupled to the target tissue.

The stimulus applied to the target tissue may include electrical stimulation of nervous tissue, also known as neuromodulation. Electrical stimulation will be described in more detail below. The stimulus may additionally or alternatively include drug stimulation. In such examples, therapeutic dosages of one or more drugs may be infused into the target tissue to treat any of a wide variety of medical conditions. Consequently, as used herein and in the appended claims, the term "stimulus" or "stimulation", unless otherwise indicated, will broadly refer to an electrical stimulation, drug stimulation, or both. The term "target tissue", as used herein and in the appended claims, refers to any tissue, nerve, organ, blood vessel, or other site within a patient to which a stimulus is applied.

In the following description, for purposes of explanation, numerous specific details are set forth in order to provide a thorough understanding of the present systems and methods. It will be apparent, however, to one skilled in the art that the present systems and methods may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
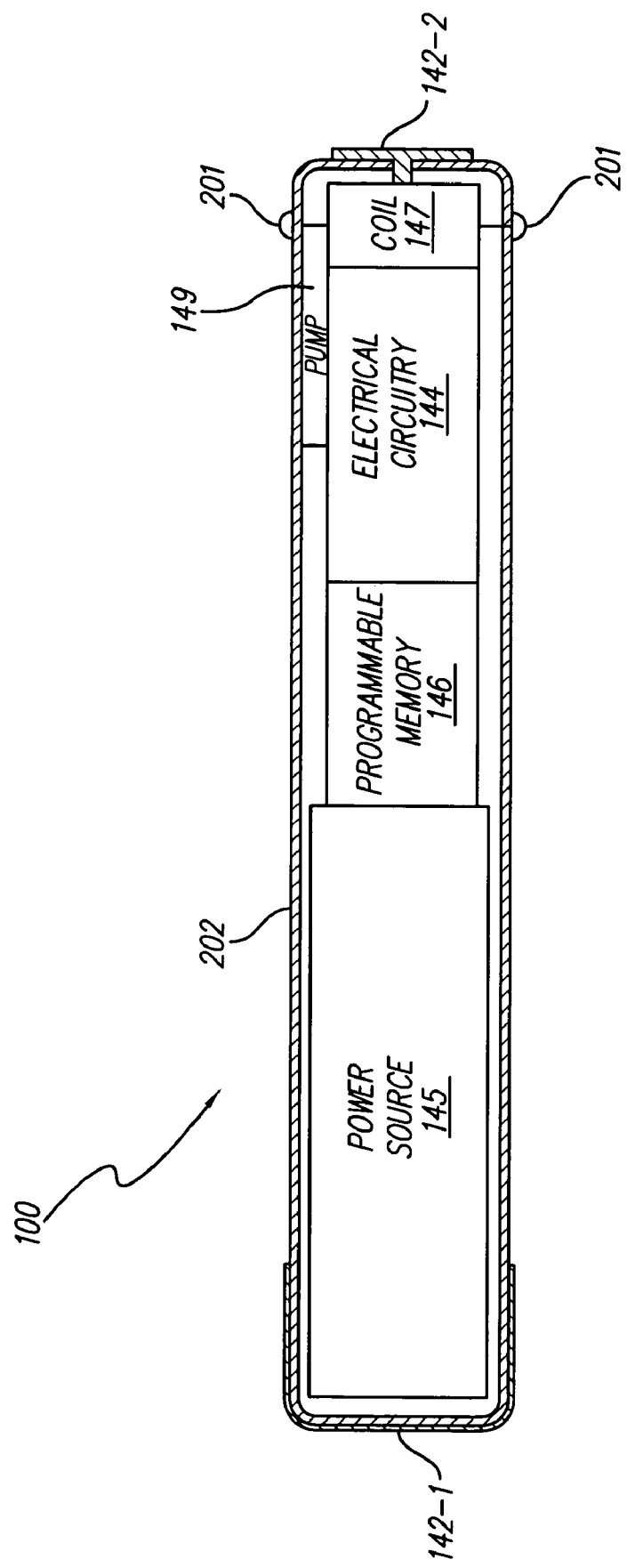
FIG. 1 illustrates an exemplary system control unit or stimulator, along with its principal components, that may be implanted within a patient and used to apply a stimulus to a target tissue to treat a particular medical condition according to principles disclosed herein.

Turning to the appended drawings, FIG. 1 illustrates an exemplary implantable SCU (100) and its principal internal and external components. This example is not to be considered as limiting in any way. Other configurations for the SCU are possible as will be described further below.

As shown in FIG. 1, the SCU (100) may include a power source (145), a programmable memory (146), electrical circuitry (144), and a coil (147). These components are housed within a capsule (202). The capsule (202) may be a thin, elongated cylinder or any other shape as best serves a particular application. The shape of the capsule (202) may be determined by the structure of the desired target tissue, the surrounding area, the method of implantation, the size and location of the power source (145) and/or the number and arrangement of external electrodes (142). In some embodiments, the capsule (202) is substantially equal to or less than three cubic centimeters.

The power source (145) is configured to output a voltage used to supply the various components within the SCU (100) with power. The power source (145) also provides power for any stimulation current applied with the SCU (100) to nearby tissue. The power source (145) may be a primary battery, a rechargeable battery, a capacitor, or any other suitable power source. Systems and methods for recharging the power source (145), where the source (145) is rechargeable, will be described below.

The coil (148) is configured to receive and/or emit a magnetic field (also referred to as a radio frequency (RF) field) that is used to communicate with or receive power from one or more external devices that support the implanted SCU (100), examples of which will be described below. Such communication and/or power transfer may include, but is not limited to, transcutaneously receiving data from the external device, transmitting data to the external device, and/or receiving power used to recharge the power source (145).

The programmable memory unit (146) is used for storing one or more sets of data, for example, stimulation parameters. The stimulation parameters may include, but are not limited to, electrical stimulation parameters and drug stimulation parameters. The programmable memory (146) allows a patient, clinician, or other user of the SCU (100) to adjust the stimulation parameters such that the electrical stimulation and/or drug stimulation are at levels that are safe and efficacious for a particular medical condition and/or for a particular patient. Electrical stimulation and drug stimulation parameters may be controlled independently. However, in some instances, the electrical stimulation and drug stimulation parameters are coupled, e.g., electrical stimulation may be programmed to occur only during drug stimulation. The programmable memory (146) may be any type of memory unit such as, but not limited to, random access memory (RAM), static RAM (SRAM), a hard drive, or the like.

The electrical stimulation parameters may control various parameters of the stimulation current applied to a target tissue including, but not limited to, the frequency, pulse width, amplitude, burst pattern (e.g., burst on time and burst off time), duty cycle or burst repeat interval, ramp on time and ramp off time of the stimulation current that is applied to the target tissue. The drug stimulation parameters may control various parameters including, but not limited to, the amount of drugs infused into the target tissue, the rate of drug infusion, and the frequency of drug infusion.

Specific electrical stimulation and drug stimulation parameters may have different effects on different types of medical conditions. Thus, in some embodiments, the electrical stimulation and/or drug stimulation parameters may be adjusted by the patient, a clinician, or other user of the SCU (100) as best serves a particular medical condition. The electrical stimulation and/or drug stimulation parameters may also be automatically adjusted by the SCU (100), as will be described below. For example, the amplitude of the stimulus current applied to a target nerve may be adjusted to have a relatively low value to target relatively large diameter fibers of the target nerve. The SCU (100) may also increase excitement of a target nerve by applying a stimulation current having a relatively low frequency to the target nerve (e.g., less than 100 Hz). The SCU (100) may also decrease excitement of a target nerve by applying a relatively high frequency to the target nerve (e.g., greater than 100 Hz). The SCU (100) may also be programmed to apply the stimulation current to a target nerve intermittently or continuously.

The SCU (100) also includes electrodes (142-1 and 142-2) on the exterior of the capsule (200). The electrodes (142) may be disposed at either end of the capsule (202), as illustrated in FIG. 1, or placed along the length of the capsule. There may also be more than two electrodes arranged in an array. One of the electrodes (142) may be designated as a stimulating electrode to be placed close to the target tissue or treatment site and one of the electrodes (142) may be designated as an indifferent electrode used to complete a stimulation circuit.

The electrical circuitry (144) is configured to produce electrical stimulation pulses that are delivered to the target nerve via the electrodes (142). In some embodiments, the SCU (100) may be configured to produce monopolar stimulation. The SCU (100) may alternatively or additionally be configured to produce bipolar stimulation. Monopolar electrical stimulation is achieved, for example, using the stimulator case (202) as an indifferent electrode. Bipolar electrical stimulation is achieved, for example, using one of the electrodes of the electrode array as an indifferent electrode.

The electrical circuitry (144) may include one or more processors configured to decode stimulation parameters and generate the corresponding stimulation pulses. In some embodiments, the SCU (100) has at least four channels and drives up to sixteen electrodes or more. The electrical circuitry (144) may include additional circuitry such as capacitors, integrated circuits, resistors, coils, and the like configured to perform a variety of functions as best serves a particular application.

In the example illustrated in FIG. 1, the SCU (100) includes two or more leadless electrodes (142). However, either or both of the electrodes (142) may alternatively be located at the ends of short, flexible leads as described in U.S. Pat. application Ser. No. 09/624,130, filed Jul. 24, 2000, which is incorporated herein by reference in its entirety. The use of such leads permits, among other things, electrical stimulation to be directed more locally to targeted tissue(s) a short distance from the surgical fixation of the bulk of the SCU (200), while allowing most elements of the SCU (200) to be located in a more surgically convenient site. This minimizes the distance traversed and the surgical planes crossed by the SCU (200) and any lead(s).

The external surfaces of the SCU (100) may advantageously be composed of biocompatible materials. For example, the capsule (202) may be made of glass, ceramic, metal, or any other material that provides a hermetic package that will exclude water vapor but permit passage of electromagnetic fields used to transmit data and/or power. The electrodes (142) may be made of a noble or refractory metal or compound, such as platinum, iridium, tantalum, titanium, titanium nitride, niobium or alloys of any of these, in order to avoid corrosion or electrolysis which could damage the surrounding tissues and the device.

The SCU (100) may also include one or more infusion outlets (201). The infusion outlets (201) facilitate the infusion of one or more drugs into the target tissue. The infusion outlets (201) may dispense one or drugs directly to the target tissue. Alternatively, catheters may be coupled to the infusion outlets (201) to deliver the drug therapy to target tissue some distance from the body of the SCU (100).

If the SCU (100) is configured to provide a drug stimulation using, for example, infusion outlets (201), the SCU (100) may also include a pump (149) that is configured to store and dispense the one or more drugs. As indicated, the pump (149) may dispense the drug therapy through the infusion outlets (201) in the casing (202) of the SCU (100) or may dispense drugs through catheters connected to those infusion outlets (201). In some examples, the SCU (100) may include multiple pumps for storing and infusing dosages of the one or more drugs used to treat that particular patient's condition.

The pump or controlled drug release device described herein may include any of a variety of different drug delivery systems. Controlled drug release devices based upon a mechanical or electromechanical infusion pump may be used. In other examples, the controlled drug release device can include a diffusion-based delivery system, e.g., erosion-based delivery systems (e.g., polymer-impregnated with drug placed within a drug-impermeable reservoir in communication with the drug delivery conduit of a catheter), electrodiffusion systems, and the like. Another example is a convective drug delivery system, e.g., systems based upon electroosmosis, vapor pressure pumps, electrolytic pumps, effervescent pumps, piezoelectric pumps and osmotic pumps.

Exemplary pumps or controlled drug release devices suitable for use as described herein include, but are not necessarily limited to, those disclosed in U.S. Pat. Nos. 3,760,984; 3,845,770; 3,916,899; 3,923,426; 3,987,790; 3,995,631; 3,916,899; 4,016,880; 4,036,228; 4,111,202; 4,111,203; 4,203,440; 4,203,442; 4,210,139; 4,327,725; 4,360,019; 4,487,603; 4,627,850; 4,692,147; 4,725,852; 4,865,845; 5,057,318; 5,059,423; 5,112,614; 5,137,727; 5,234,692; 5,234,693; 5,728,396; 6,368,315 and the like. All of these listed patents are incorporated herein by reference in their respective entireties.

The SCU (100) of FIG. 1 is illustrative of many types of SCUs that may be used to apply electrical stimulation to target tissue and/or infuse one or more drugs into the target tissue to treat a particular medical condition. The following listed patents describe various details associated with the manufacture, operation, and use of SCUs or BION implantable microstimulators, and are all incorporated herein by reference in their respective entireties:

| Application/Patent/ Publication No. | Filing/Publication Date | Title |
| --- | --- | --- |
| U.S. Pat. No. 5,193,539 | Issued Mar. 16, 1993 | Implantable Microstimulator |
| U.S. Pat. No. 5,193,540 | Issued Mar. 16, 1993 | Structure and Method of Manufacture of an Implantable Microstimulator |
| U.S. Pat. No. 5,312,439 | Issued May 17, 1994 | Implantable Device Having an Electrolytic Storage Electrode |
| U.S. Pat. No. 6,185,452 | Issued Feb. 6, 2001 | Battery-Powered Patient Implantable Device |

-continued

| Application/Patent/<br>Publication No. | Filing/Publication<br>Date | Title |
|---|---|---|
| U.S. Pat. No. 6,164,284 | Issued Dec. 26, 2000 | System of Implantable Devices For Monitoring and/or Affecting Body Parameters |
| U.S. Pat. No. 6,208,894 | Issued Mar. 27, 2001 | System of Implantable Devices For Monitoring and/or Affecting Body Parameters |
| U.S. Pat. No. 6,051,017 | Issued Apr. 18, 2000 | Implantable Microstimulator and Systems Employing Same |

Figure 2:
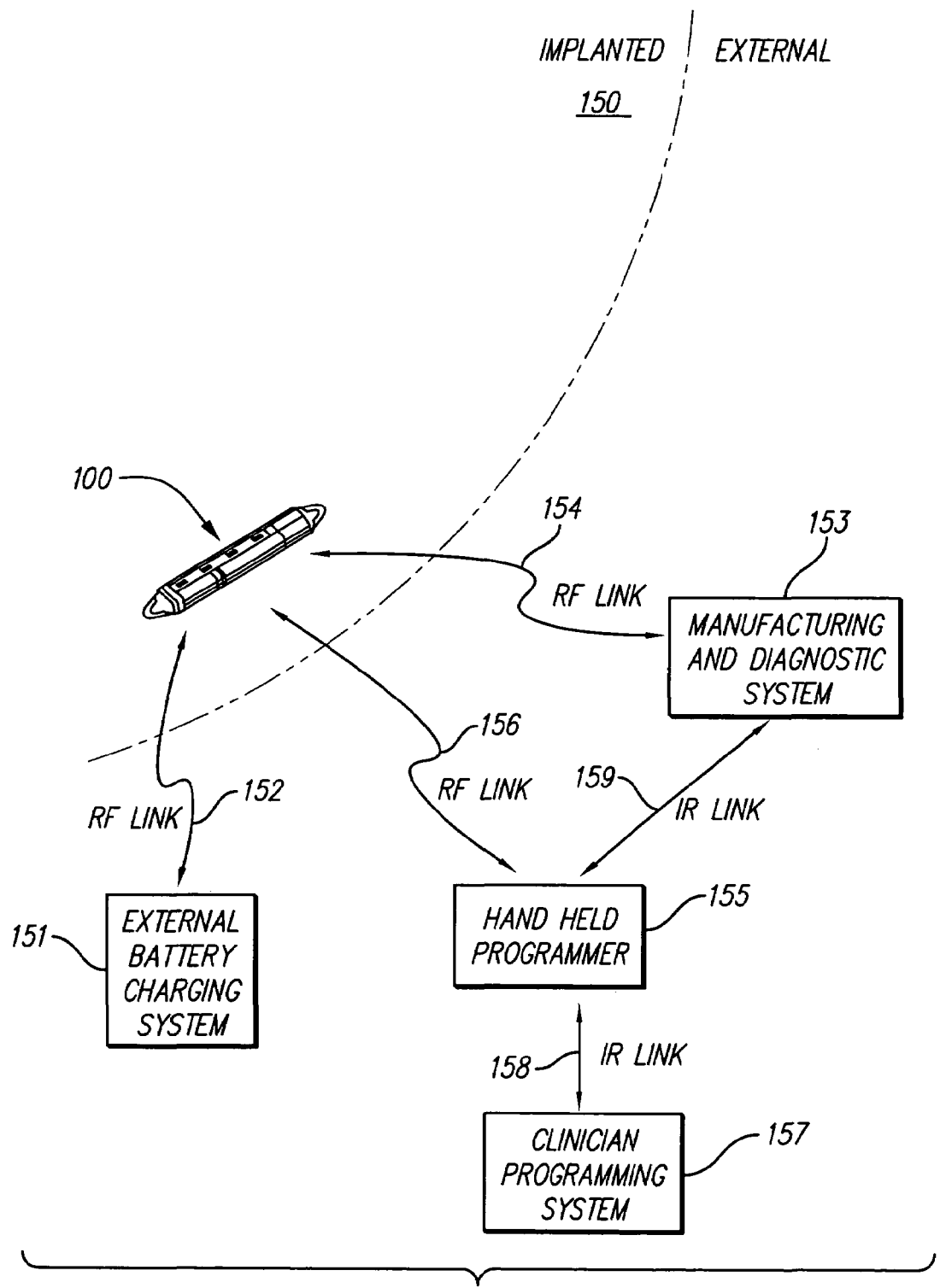
FIG. 2 illustrates an exemplary system control unit (SCU) and various examples of the external devices that may be used to support the implanted SCU according to principles described herein.

Turning to FIG. 2, FIG. 2 illustrates an exemplary implanted SCU (100) and examples of the various systems and external devices that may be used to support the implanted SCU (100). For example, an external battery charging system (EBCS) (151) may provide power used to recharge the power source (145, FIG. 1) via an RF link (152). External devices including, but not limited to, a hand held programmer (HHP) (155), clinician programming system (CPS) (157), and/or a manufacturing and diagnostic system (MDS) (153) may be configured to activate, deactivate, program, and test the SCU (100) via one or more RF links (154, 156). One or more of these external devices (153, 155, 157) may also be used to control the SCU (100) to provide stimulation electrical pulses or an infusion of one or more drugs into target tissue to treat a particular medical condition. The external devices (153, 155, 157) may be used to provide or update the stimulation parameters and other data stored in the programmable memory (146, FIG. 1) of the SCU (100).

In some cases, there two or more of the various illustrated external devices (153, 155, 157) may be used in the treatment of a particular implant patient (150). If multiple external devices are used in the treatment of a patient, there may be some communication among those external devices, as well as with the implanted SCU (100). For example, the CPS (157) may communicate with the HHP (155) via an infrared (IR) link (158) or via any other suitable communication link. Likewise, the MDS (153) may communicate with the HHP (155) via an IR link (159) or via any other suitable communication link.

The HHP (155), MDS (153), CPS (157), and EBCS (151) are merely illustrative of the many different external devices that may be used in connection with the SCU (100). Furthermore, it will be recognized that the functions performed by the HHP (155), MDS (153), CPS (157), and EBCS (151) may be performed by a single external device. One or more of the external devices (153, 155, 157) may be embedded in a seat cushion, mattress cover, pillow, garment, belt, strap, pouch, or the like, so as to be conveniently placed near the implanted SCU (100) when in use.

The SCU (100) of FIG. 2 may be configured to operate independently. Alternatively, as will be described in more detail below, the SCU (100) may be configured to operate in a coordinated manner with one or more additional SCUs, other implanted devices, or other devices external to the patient's body.

In order to determine the amount and/or type(s) of stimulating drug(s) and/or the strength and/or duration of electrical stimulation required to most effectively treat a particular medical condition, various indicators of the medical condition and/or a patient's response to treatment may be sensed or measured. These indicators include, but are not limited to, muscle or limb activity (e.g., electromyography (EMG)), electrical activity of the brain (e.g., EEG), neurotransmitter levels, hormone levels, and/or medication levels. In some embodiments, the SCU (100) may be configured to change the stimulation parameters in a closed loop manner in response to these measurements. The SCU (100) may be configured to perform the measurements. Alternatively, other sensing devices may be configured to perform the measurements and transmit the measured values to the SCU (100).

Thus, it is seen that one or more external appliances may be provided to interact with the SCU (100), and may be used to accomplish at least one or more of the following functions:

Function 1: If necessary, transmit electrical power to the SCU (100) in order to power the SCU (100) and/or recharge the power source (145, FIG. 1).

Function 2: Transmit data to the SCU (100) in order to change the stimulation parameters used by the SCU (100).

Function 3: Receive data indicating the state of the SCU (100) (e.g., battery level, drug level, stimulation parameters, etc.).

Additional functions may include adjusting the stimulation parameters based on information sensed by the SCU (100) or by other sensing devices.

By way of example, an exemplary method of treating a particular medical condition within a patient may be carried out according to the following sequence of procedures. The steps listed below may be modified, reordered, and/or added to as best serves a particular application.

1. An SCU (100) is implanted so that its electrodes (142, FIG. 1) and/or infusion outlet (201, FIG. 1) are coupled to or located near a target tissue. If the SCU (100) is a microstimulator, such as the BION microstimulator, the microstimulator itself may be coupled to the target tissue.

2. The SCU (100) is programmed to apply at least one stimulus to the target tissue. The stimulus may include electrical stimulation and/or drug stimulation.

3. When the patient desires to invoke electrical and/or drug stimulation, the patient sends a command to the SCU (100) (e.g., via a remote control) such that the SCU (100) delivers the prescribed electrical and/or drug stimulation. The SCU (100) may be alternatively or additionally configured to automatically apply the electrical and/or drug stimulation in response to sensed indicators of the particular medical condition.

4. To cease electrical and/or drug stimulation, the patient may turn off the SCU (100) (e.g., via a remote control).

5. Periodically, the power source (145, FIG. 1) of the SCU (100) is recharged, if necessary, in accordance with Function 1 described above.

For the treatment of any of the various types of medical conditions, it may be desirable to modify or adjust the algorithmic functions performed by the implanted and/or external components, as well as the surgical approaches. For example, in some situations, it may be desirable to employ more than one SCU (100), each of which could be separately controlled by means of a digital address. Multiple channels and/or multiple patterns of electrical and/or drug stimulation may thereby be used to deal with multiple medical conditions.

Figure 3:
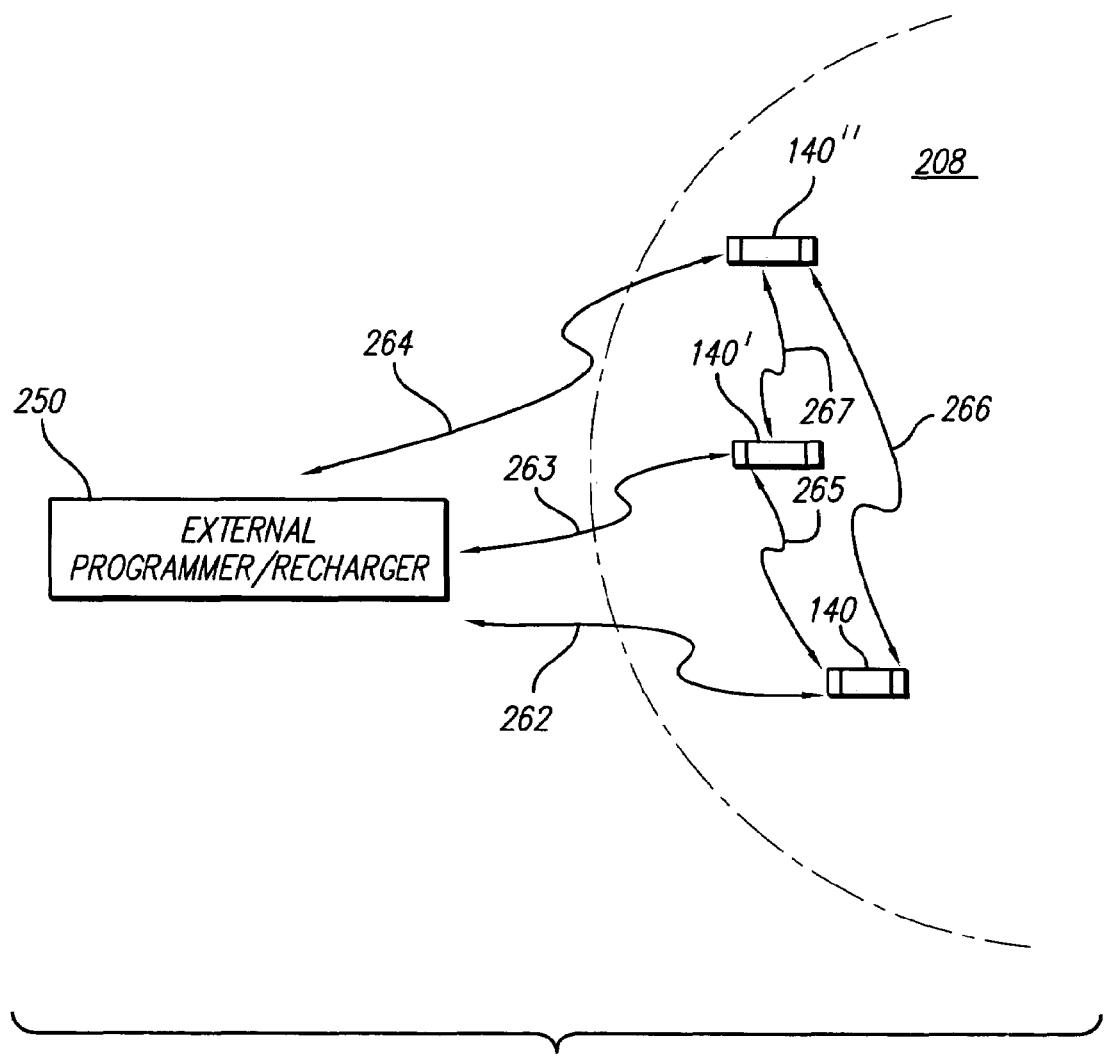
FIG. 3 illustrates a number of SCUs implanted in a patient according to principles described herein and working in conjunction for the treatment of that patient.

For instance, as shown in the example of FIG. 3, a first SCU (100) implanted beneath the skin (208) of the patient provides a stimulus to a first location; a second SCU (140') provides a stimulus to a second location; and a third SCU (140") provides a stimulus to a third location. As mentioned earlier, the implanted devices may operate independently or may operate in a coordinated manner with other implanted devices or other devices external to the patient's body. That is, an external controller (250) may be configured to control the operation of each of the implanted devices (140, 140', and 140"). In some embodiments, an implanted device, e.g. SCU (100), may control or operate under the control of another implanted device(s), e.g. SCU (140') and/or SCU (140"). Control lines (262-267) have been drawn in FIG. 3 to illustrate that the external controller (250) may communicate or provide power to any of the implanted devices (140, 140', and 140") and that each of the various implanted devices (140, 140', and 140") may communicate with and, in some instances, control any of the other implanted devices.

As a further example of multiple SCUs (100) operating in a coordinated manner, the first and second SCUs (140, 140') of FIG. 3 may be configured to sense various indicators of a particular medical condition and transmit the measured information to the third SCU (140"). The third SCU (140") may then use the measured information to adjust its stimulation parameters and apply electrical and/or drug stimulation to a target nerve accordingly.

Alternatively, the external device (250) or other external devices communicating with the external device may be configured to sense various indicators of a patient's condition. The sensed indicators can then be transmitted to the external device (250) or to one or more of the implanted SCUs which may adjust stimulation parameters accordingly. In other examples, the external controller (250) may determine whether any change to stimulation parameters is needed based on the sensed indicators. The external device (250) may then signal a command to one or more of the SCUs to adjust stimulation parameters accordingly. Despite the various types of microstimulators known in the art, as illustrated by the examples cited above, significant improvements are still possible and desirable, particularly relative to a microstimulator with a self-contained primary or rechargeable battery that: (a) can accommodate the various needs of a microstimulator; (b) can accommodate various locations in the implanted site; and/or (c) can allow the microstimulator to operate longer between charges or replacement.

The SCU (100) of FIGS. 1 and 2 may be implanted within the patient (150) using any suitable surgical procedure such as, but not limited to, injection, small incision, open placement, laparoscopy, or endoscopy. The SCU (100) may be implanted within a patient with a surgical tool such as a hypodermic needle, bore needle, or any other tool specially designed for the purpose. In general, the SCU (100) is implanted with a tool that is used to push the SCU (100) through a needle, cannula or incision to a position proximate to the target tissue to be stimulated.

For example, a tool used to implant an SCU (100) may be an elongated, tubular, rigid or semi-rigid tool with a handle at one end and some mechanism at the tip for engaging the SCU. The engagement mechanism at the tip holds the SCU in place on the tool until released. With the SCU engaged by the tool, the tool is used to push the SCU into place.

It may be difficult, however, to accurately position the SCU with this push insertion method. The clinician placing the SCU often pushes the SCU through resistive tissue using the handle of the insertion tool. Any slight movement of the hand during this procedure can produce a significant direction shift at the tool tip, possibly resulting in a placement of the SCU relatively distant from a desired implant location and target tissue.

Additionally, when the SCU is finally positioned, the mechanism engaging the SCU is released. The act of releasing the SCU may also affect the position of the SCU. If the position of the SCU shifts after the tool has been disengaged, it is very difficult to reposition the SCU.

There are locations in the human body where an SCU would be implanted, for example, in a limb or in the neck, where a needle or other member can be inserted, passed proximal to the target tissue to be stimulated and then exit through the skin. This member can also be attached to the SCU and used to pull the SCU into place proximal to the target tissue to be stimulated. The member may be, for example, a rod, a needle, an elongated tool, a line or any other device that can attach to the SCU and be used to pull the SCU into place.

As mentioned, in some examples, the member is a line that can be attached to a pass-through needle so as to then pass through the patient proximal to the target tissue for stimulation. An SCU is then attached to this line which is used to pull the SCU into place proximal to the target tissue to be stimulated within the patient. This process will be illustrated and described in detail below.

Figure 4:
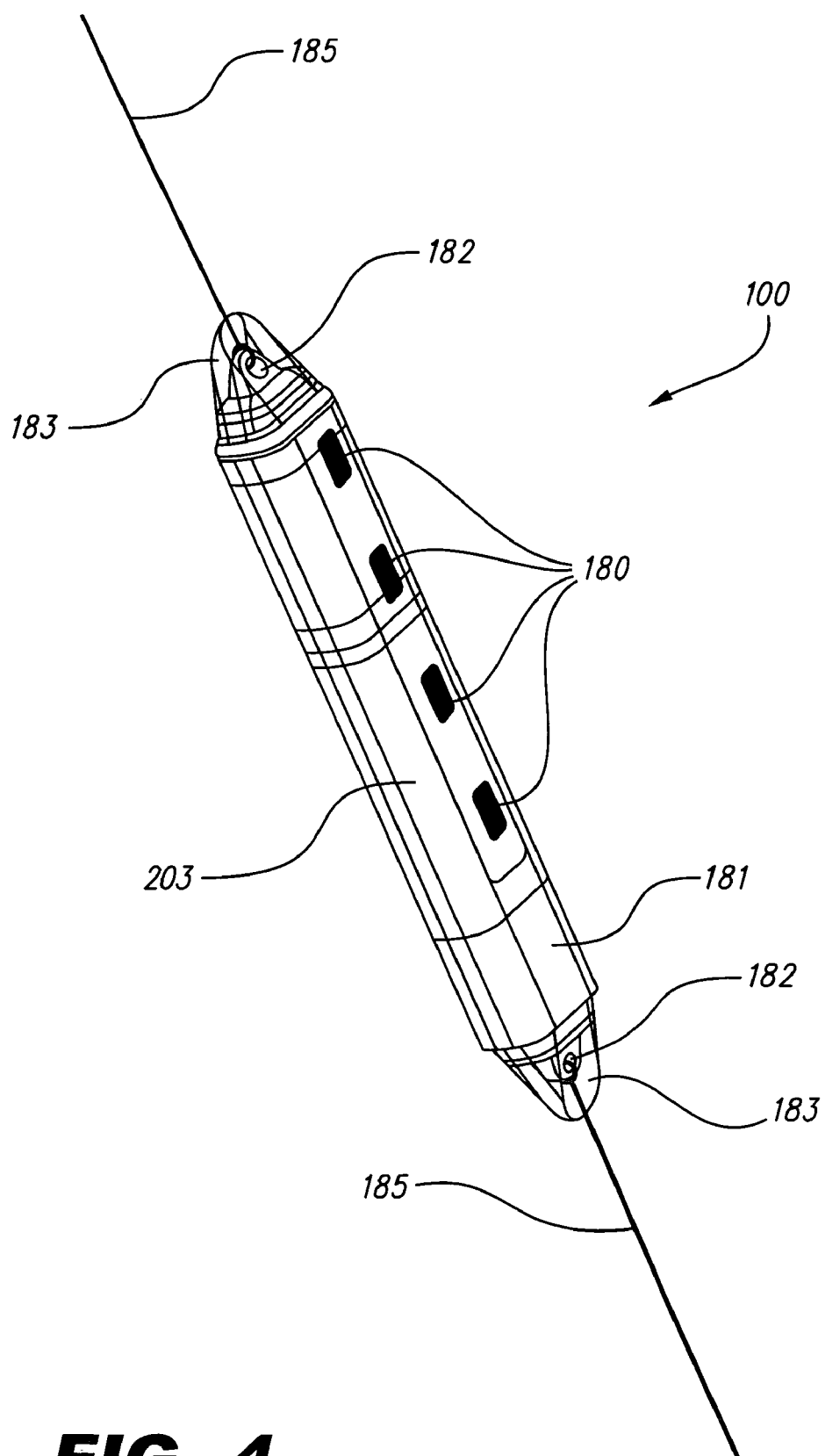
FIG. 4 illustrates an exemplary SCU according to principles described herein which is adapted to be easily and readily positioned at an optimal location in a patient according to principles described herein.

Turning to FIG. 4, an SCU (100) is shown that can be more easily and accurate positioned as described herein. As shown in FIG. 4, the SCU (100) has an elongated body on which, for example, a number of electrodes (180) are placed for providing an electrical stimulation as described herein. The SCU (100) may also provide a drug stimulation as described above.

The number of electrodes (180) in the illustrated example is four. However, it will be understood that more or fewer electrodes may be used. As shown in the illustration, a side of the SCU casing (203) may be relatively flat for supporting the electrodes (180). The casing (203) of the SCU (100) may also include an indifferent electrode (181) for completing a stimulation circuit with any or all of the active electrodes (180).

At either end of the casing (203) an eyelet (182) is formed. A line (185) is then attached to the eyelet (182) at either or both ends of the SCU (100). This line may be any line that can be pulled through a portion of a patient's body and then used to position the SCU (100) as described herein. For example, the line (185) may be, but is not limited to, a string, a suture line, a silk line, a wire, a filament and the like. In some examples, the line is dissolvable, meaning that the line will naturally dissolve if left in the patient's tissue.

Alternative to the eyelets (182), any other means of attaching or anchoring the line (185) to the SCU (100) may be used. For example, the line may be tied to the eyelet (182), integrated into the material of the casing (203), tacked or adhered to the casing (203), etc.

Each attachment point of the line (185) to the SCU (100) may be encapsulated. For example, a polymer cap (183) of, for example, silicone may be placed over the attachment points where the line (185) is secured to the SCU (100). Either end of the SCU (100) may have a relatively sharp point thereon to separate or cut through tissue as the SCU (100) is pulled into place so as to allow passage of the SCU (100) without unnecessary tissue damage. Alternatively, a sharp or pointed device may be added to, or threaded on, the line (185) to separate cut through tissue as the SCU (100) is pulled into place, again, to allow passage of the SCU (100) without unnecessary tissue damage.

Figure 5:
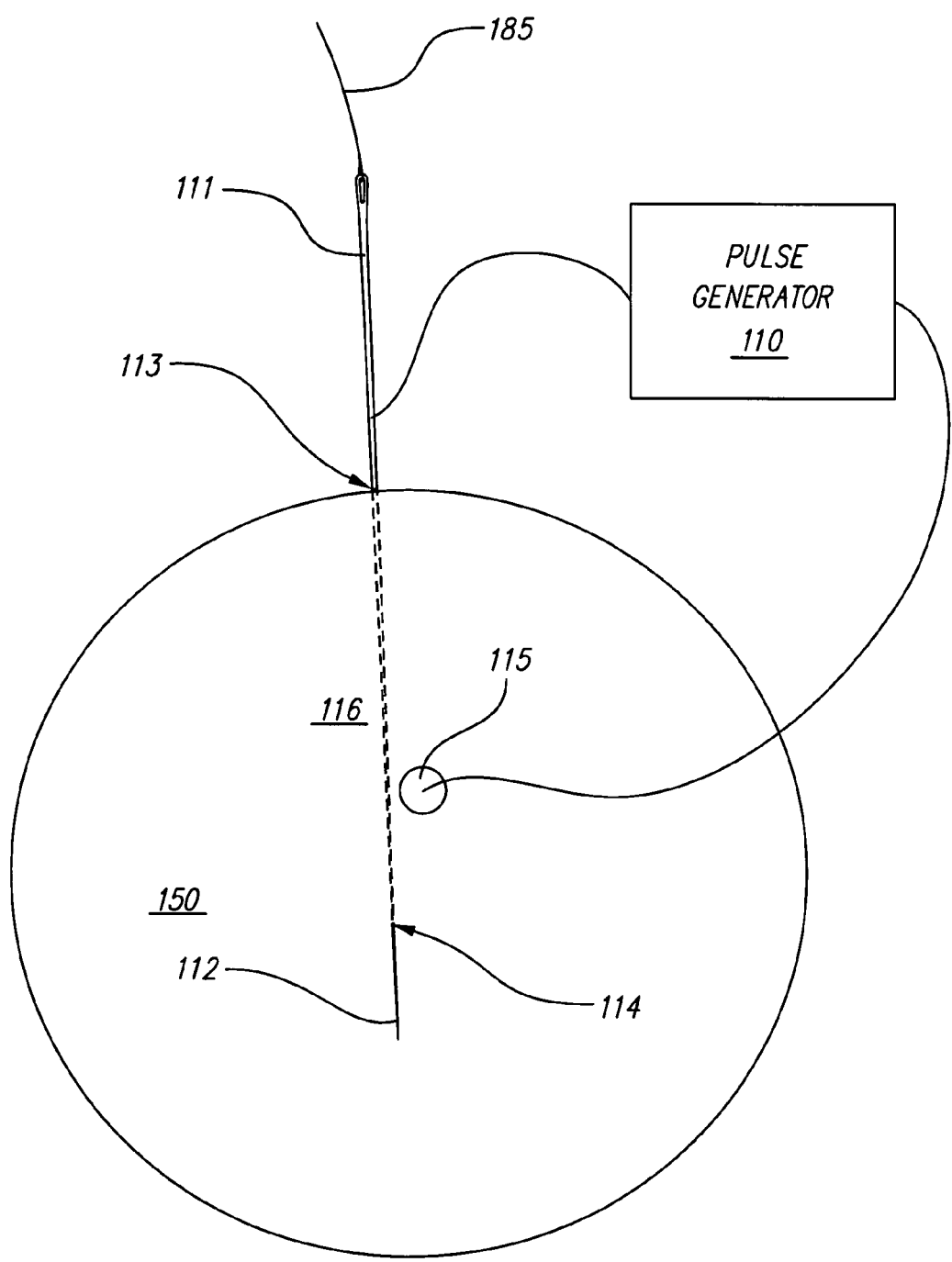
FIGS. 5-7 illustrated various steps in an exemplary method of implanting an SCU proximal to a target tissue according to principles described herein.
Figure 6:
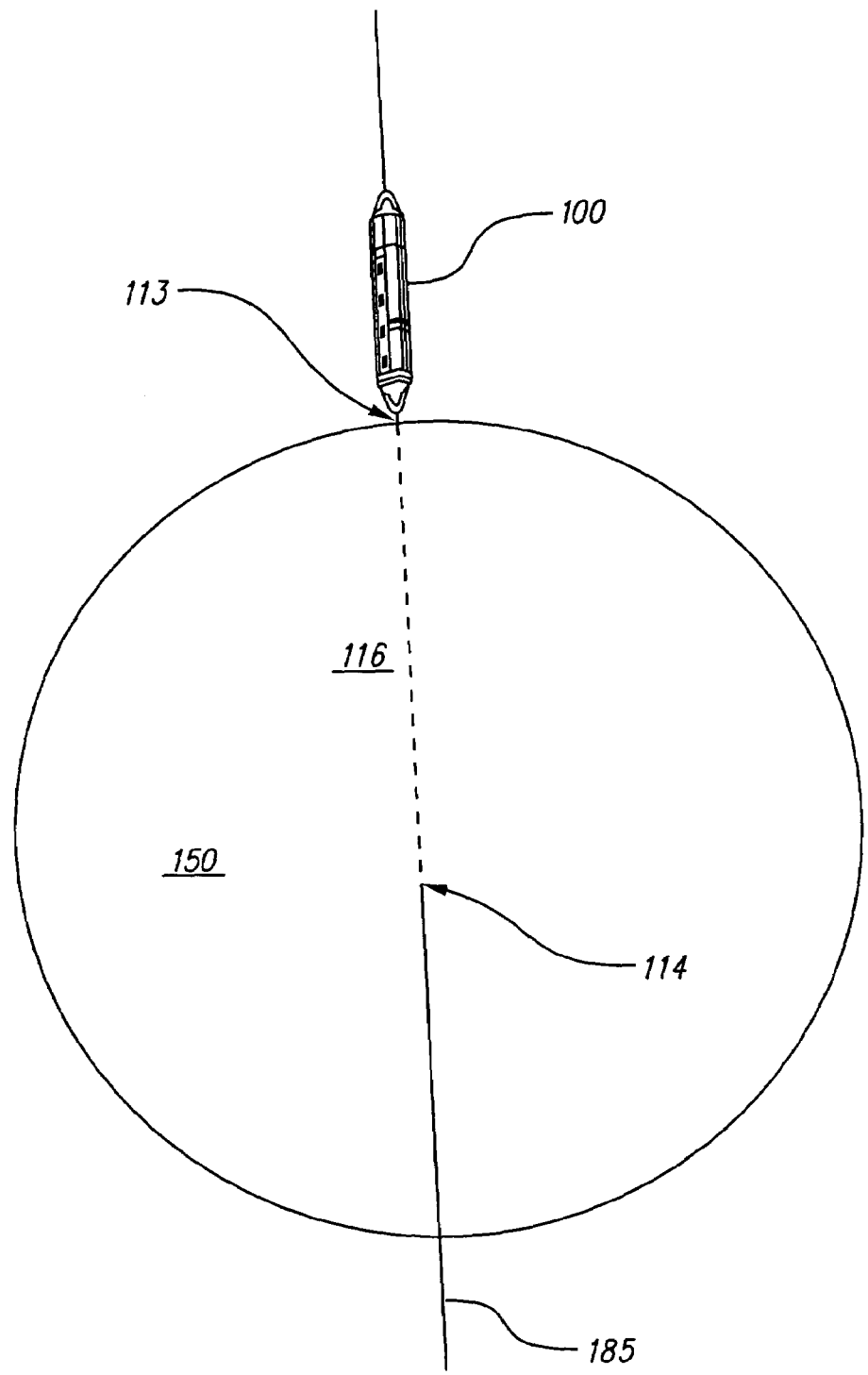

A method of implanting the SCU (100) of FIG. 4 will now be described with reference to FIGS. 5-7. In FIG. 5, the body (150) represents a portion of the human body where tissue targeted for stimulation is located between a needle insertion point and a needle exit point as will be described herein. Consequently, the body (150) may represent, for example, a patient's neck or limb or some other location relatively near the surface under a patient's skin.

As shown in FIG. 5, a needle (111), to which the line (185) is attached, has a sharp tip (112) that is threaded through the patient's body between an insertion point (113) and an exit point (114). The needle (111) is inserted through an insertion point (113) in the patient's body (150). The needle (111) is then passed proximal to the tissue (116) that is targeted for stimulation. The tip (112) of the needle (111) then exits the patient's body (150) through an exit point (114).

As the needle (111) is threaded between the insertion point (113) and exit point (114), it may be useful to confirm that the needle (111) has been inserted proximal to the target tissue (116) as intended. Consequently, an electrical pulse generator (110) may be electrically connected to the needle (111) as shown in FIG. 5. The pulse generator (110) is also connected to an indifferent electrode (115) that may be placed on the patient's skin near to the target tissue (116).

The pulse generator (110) is then used to provide an electrical stimulation pulse through the needle (111) to the target tissue (116). The needle (111) is made of metal or some other electrically conductive material so as to conduct the electrical stimulation pulse from the pulse generator (110). In some examples, most of the length of the needle is covered with an insulating material and only the tip (112) delivers the electrical stimulation pulse to the surrounding tissue. If the needle (111) is properly placed, the stimulation pulse from the pulse generator (110) will cause a predictable effect that should result from stimulation of the target tissue (116), for example, a paresthesia. The patient can be questioned or otherwise monitored as to the effect created by the pulse generator (110) so as to confirm the proper placement of the needle (111). In this way, it can be ascertained that the needle (111) has been inserted proximal to the tissue (116) to be stimulated.

The needle (111) is then pulled through the exit point (114) leaving the line (185) threaded through the body (150) and running next to the target tissue (116). As shown in FIG. 6, the SCU (100) is attached to the line (185) outside the insertion point (113). The portion of the line (185) extending from the exit point (114) is then pulled to pull the SCU (100) though the insertion point (113) and through the patient's body (150) to a position proximal to the tissue (116) targeted for stimulation.

Figure 7:
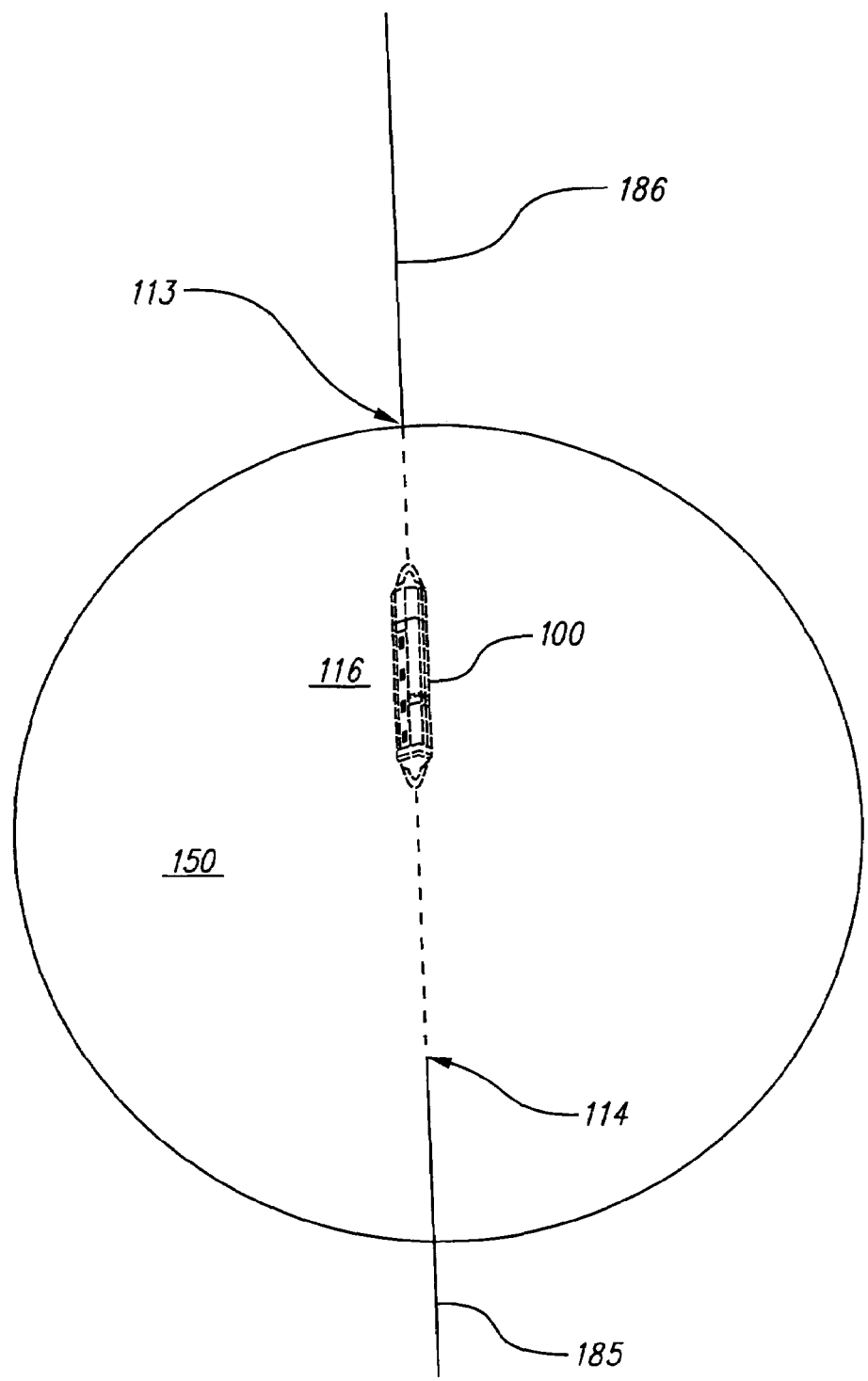

FIG. 7 illustrates the SCU (100) positioned inside the body (150) proximal to the tissue (116) targeted for stimulation. As shown in FIG. 7, a second line (186) is attached to the other end of the SCU (100) and extends from the insertion point (113) even after the SCU (100) has been pulled into the patient's body (150). Consequently, if the SCU (100) is pulled too far into the patient's body (150) using the line (185) extending from the exit point (114), past the tissue (116) targeted for stimulation, the clinician placing the SCU (100) can pull the SCU (100) back into the optimal placement by pulling on the second line (186). In fact, the clinician can pull on either line (186, 185) as needed, with a flossing action, to determine and obtain the optimal placement for the SCU (100). During this process, the SCU (100) may be active and providing an electrical stimulation about which the patient can be questioned or monitored to determine the most efficacious placement for the SCU (100).

Figure 8:
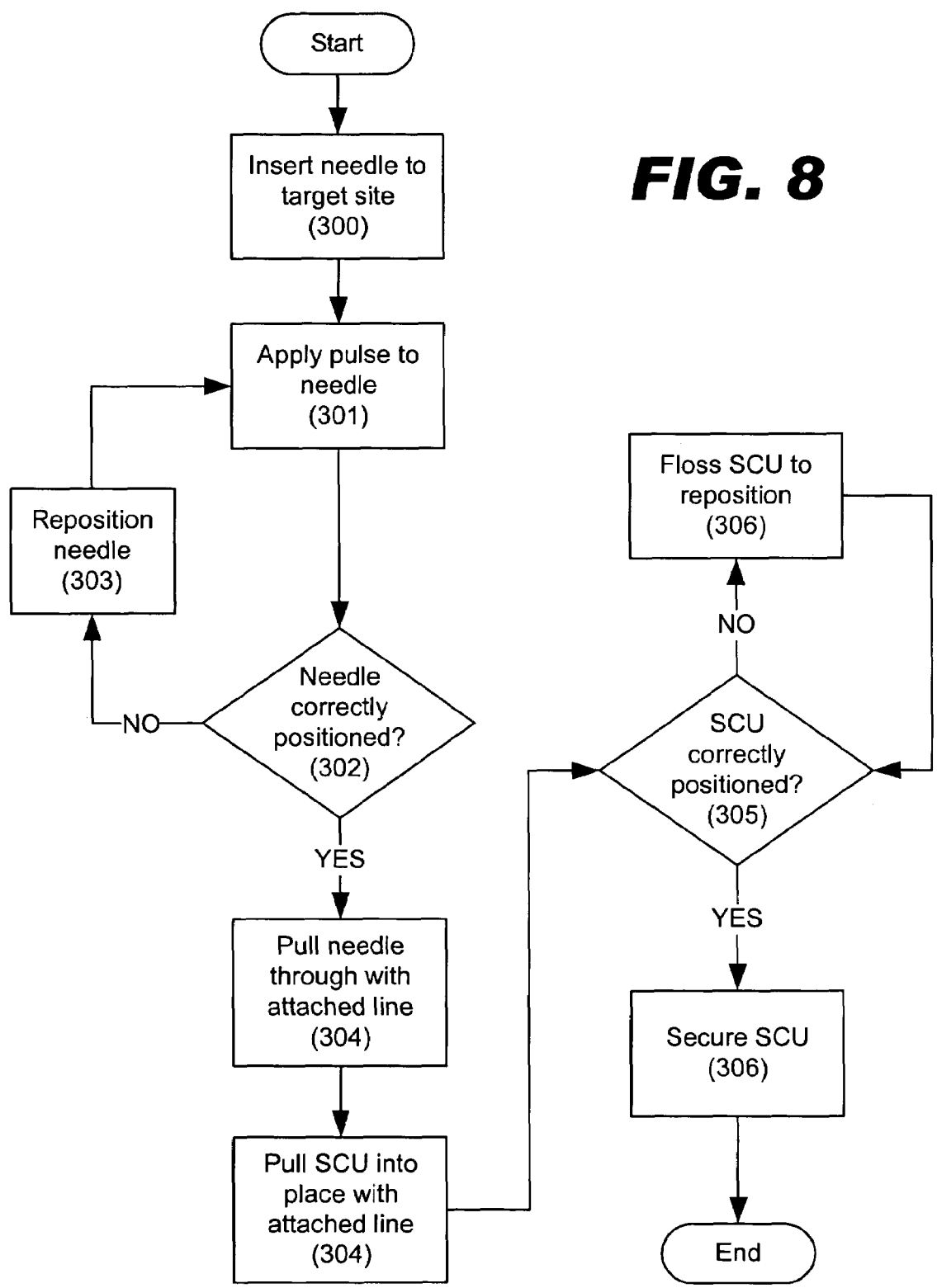
FIG. 8 is a flowchart further illustrating the exemplary method illustrated in FIGS. 5-7 and according to principles described herein.

FIG. 8 is a flowchart illustrated an example of the method described above with respect to FIGS. 5-7. As shown in FIG. 8, a pull-through needle is first inserted at the target site (step 300). The needle is inserted so as to be pass proximal to the tissue to be stimulated and through a location where the SCU is optimally placed. To determine if the needle has been inserted as intended, a series of pulses or stimulation current may be applied to the needle (step 301). This may be done with the pulse generator and indifferent electrode described above.

By gauging the effect of the electric stimulation delivered via the needle, it can be determined if the needle was positioned within the patient as intended (determination 302). If not, the needle is repositioned (step 303), and the test stimulation is repeated.

Once the needle is confirmed as having passed proximal to the tissue to be stimulated and through the desired site for the SCU, the needle is pulled through an exit point in the patient's skin (step 304). A line is attached to the needle and follows the needle through the patient's body between the insertion point and exit point.

The SCU being implanted is attached to this line and pulled into place using the line extending from the needle exit point, as illustrated above (step 304). A second line is attached to the SCU and continues to extend out through the needle insertion point.

The effect of the SCU can then be gauged to determine whether the SCU is, in fact, optimally placed within the patient (determination 305). If the SCU is not optimally placed, the lines extending from the needle insertion and exit points can be selectively pulled to "floss" the SCU into the optimal location.

Once the SCU is optimally positioned (determination 305), the SCU is secured at that location. Any implantation tools, imaging tools or other structures that may be in use can be removed while the SCU is held in place by the lines. The SCU can then be secured in place, for example, by suturing or otherwise securing or adhering the lines attached to the SCU at both the needle insertion point and the needle exit point. In this way, the SCU will be held at the desired location. Over time, tissue will grow around the SCU securing it at the desired location. As a result, the SCU is easily placed at a desired target location with great precision and using a minimally invasive procedure.

Additionally, as described above, the lines attached to the SCU may be dissolvable so as to naturally disintegrate with time in the patient's body. Alternatively, once the SCU is optimally positioned, the lines used for positioning the SCU could be cut at the insertion and exit points, and left inside the patient's body. These remaining lines extending to near the patient's skin and still attached to the SCU may be a useful instrument if the SCU is ever to be explanted from the body. The SCU can be readily located using the lines used to position the SCU initially. In some examples, a radio opaque bead could also be attached to the end of each near the patient's skin to further facilitate the location and explantation of the SCU.

The forgoing method has been described with reference to the SCU of FIG. 4, for example, and the like, where the electrodes of the SCU are disposed on the body or casing of the SCU. However, it will be understood by those skilled in the art that the same method using a pull-through needle and a line or flossing lines could be applied to position a lead extending from an SCU, a catheter extending from an SCU and/or an SCU body having a lead or catheter extending therefrom.

As described above, the principles described herein are particularly well suited for optimally placing an SCU along a straight linear path through a patient's body. Additionally, the principles described herein can be used to place an SCU along a curved or angled path through a patient's body using an anchor point such as a pivot tool, hook, eyelet or the like.

Figure 9:
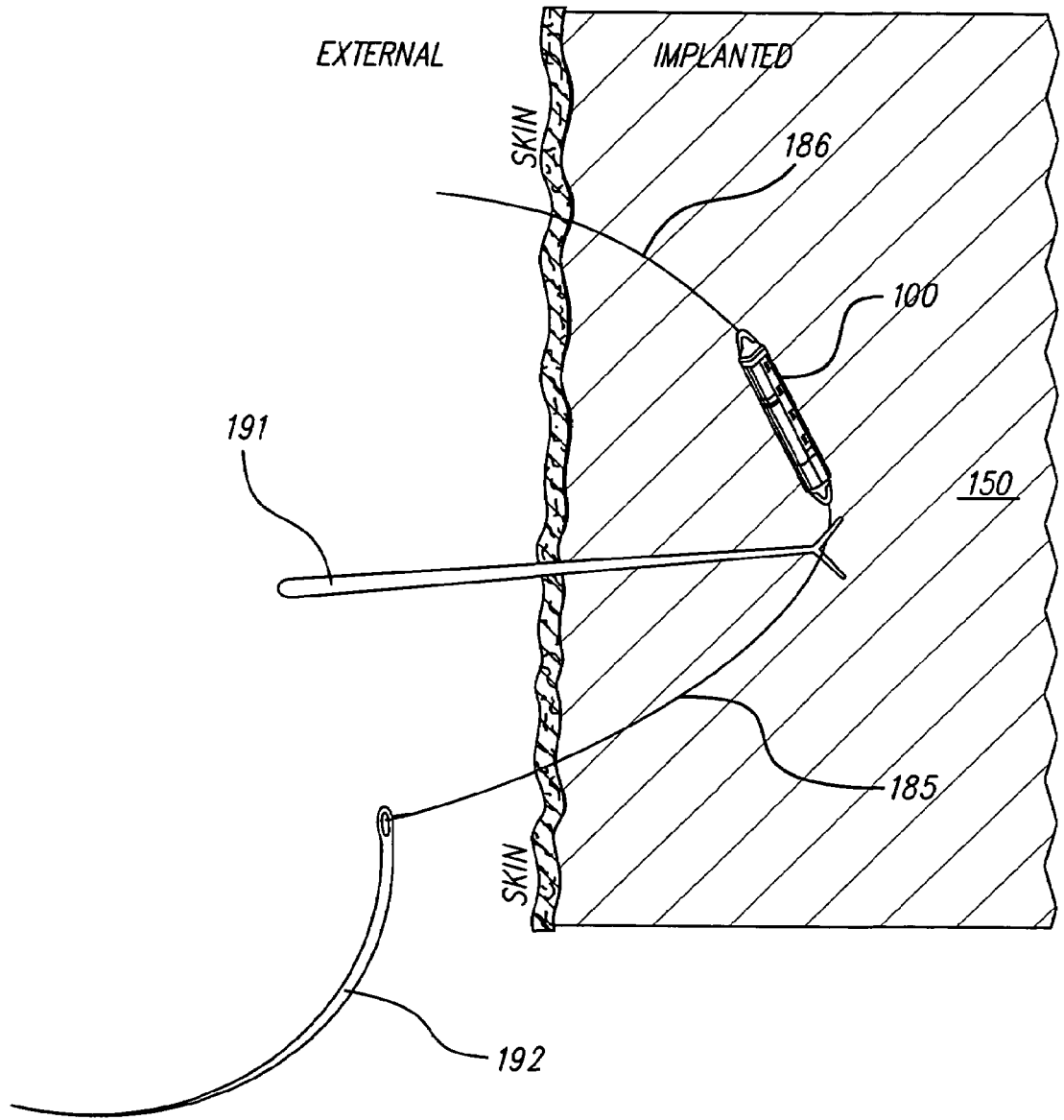
FIG. 9 illustrates a method of placing an implanted SCU along a curved path according to principles described herein.

FIG. 9 illustrates one such technique. As shown in FIG. 9, a pivot tool (191) can be inserted into a patient (150). The end of the pivot tool (191) may have a tip that includes a fork, loop, or other structure as shown in FIG. 9. This tip is placed adjacent the curved path through the patient (150) along which the SCU (100) is placed.

A curved needle (192) is then used to thread a line (185) along the curved path. As described above, the line (185) is connected to the SCU (100) to be implanted. Using the line (185), the SCU (100) is then pulled along the curved path. The line (185) will slide through the tip of the pivot tool (191). The tip of the pivot tool (191) will thereby prevent the force on the line (185) from tearing the line (185) out of the curved path along which the SCU (100) is to be placed.

A second line (186) may be attached to the rear end of the SCU (100). As described above, the SCU (100) can be pulled forward or backward along the curved path using the two lines (185, 186) so as to optimally place the SCU (100) within the patient (150).

Figure 10:
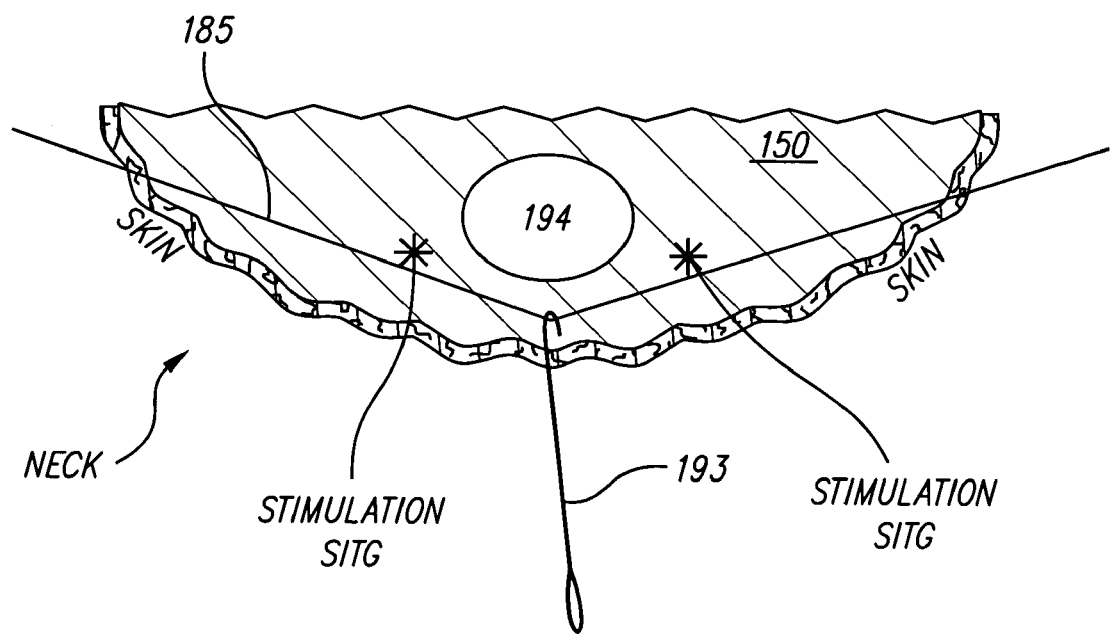
FIG. 10 illustrates another method of placing an implanted SCU along a curved path according to principles described herein.
Figure 11:
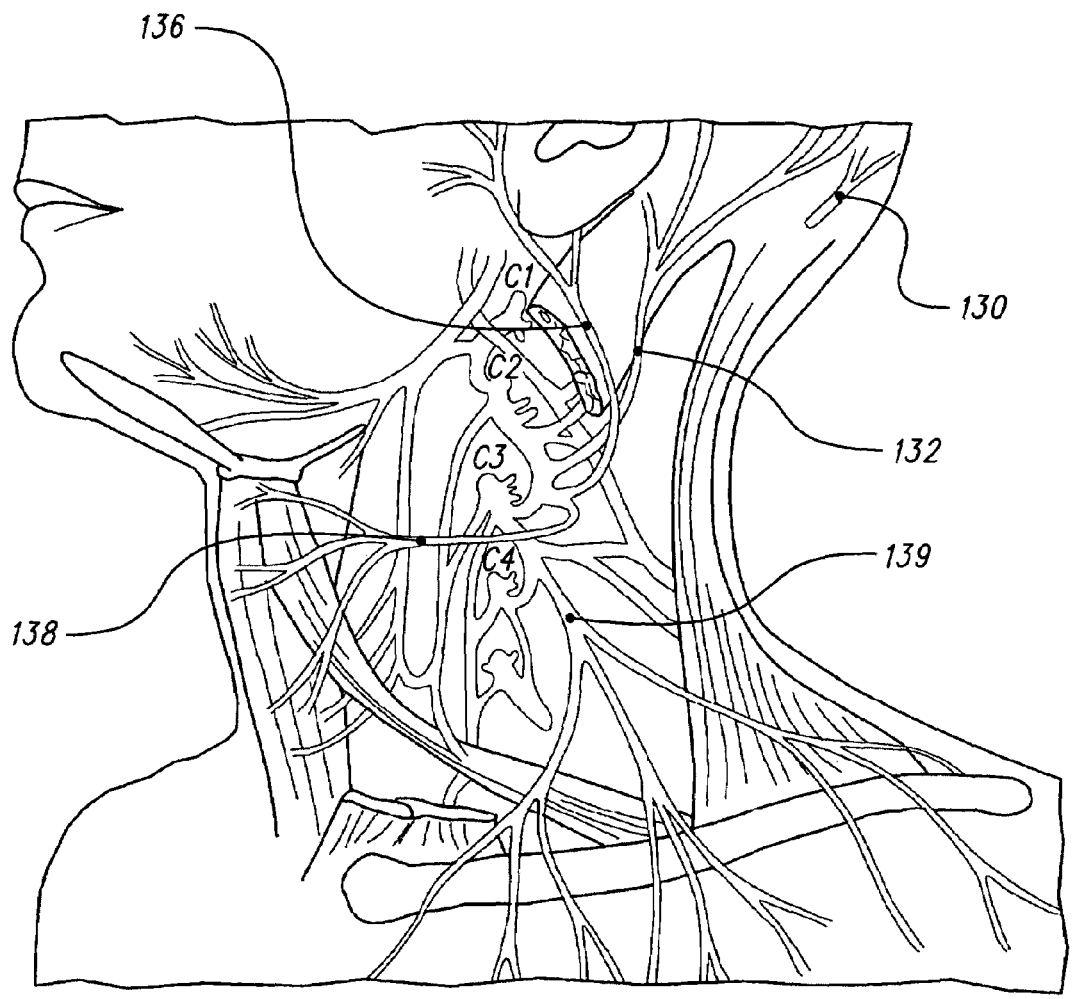
FIG. 11 depicts the upper cervical spine area of a patient and shows a number of nerves originating in the upper cervical spine area that can be target tissue for stimulation with an implanted SCU according to principles described herein.
Figure 12:
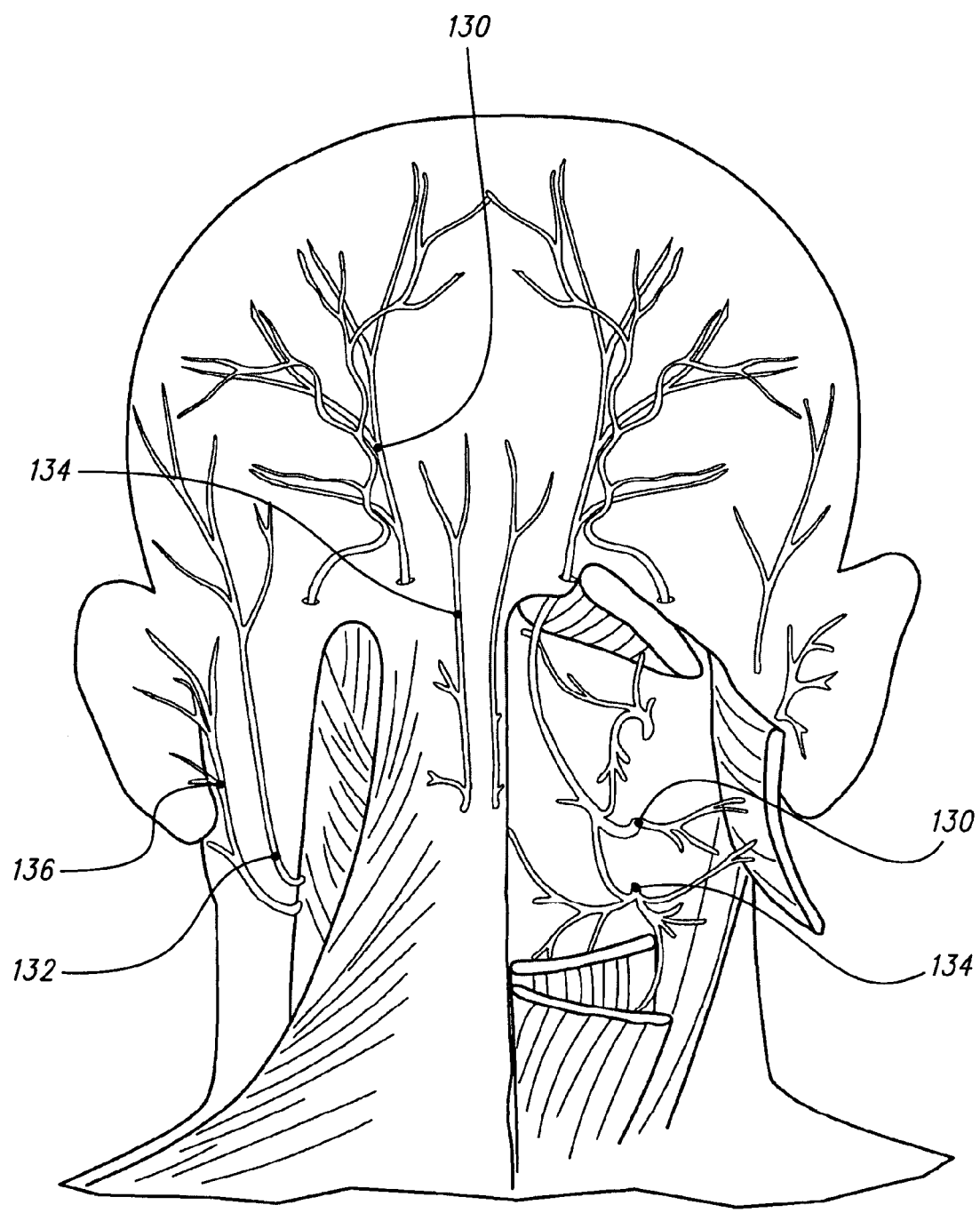
FIG. 12 shows various nerves in the back of the head and neck that can be target tissue for stimulation with an implanted SCU according to principles described herein.

FIG. 10 illustrates another technique for placing an SCU along a curved or angled path through a patient's body (150). As shown in FIG. 10, the line (185) is threaded with a curved or straight needle through a hook (193) inserted into the patient (150). This hook (193) can be pulled or held in position to provide a turning point around which the line (185) bends or angles. The hook (193) may have a hooked tip as shown in FIG. 10 or may have a tip comprising an eyelet.

The line (185) may be threaded through the hook (193), for example, by inserting the line (185) with a straight needle to a certain point and then folding or otherwise manipulating the skin of the patient so that when the needle is advanced, the path of the needle has been changed or angled with respect to the original insertion path. As shown in FIG. 10, this technique may be used to angle the line (185) around an internal structure of the patient such as the spine (194).

The SCUs described herein and the methods of optimally positioning such SCUs when implanted can be applied in the treatment of a wide variety of different medical, psychiatric, and neurological conditions and/or disorders. A number of these conditions and disorders will now be described below. However, it will be understood that this description is merely exemplary and is not limiting in any way. The SCUs and methods of optimally placing the SCU described herein may be used to treat any condition or disorder where stimulation from an implanted SCU is helpful to treat the symptoms or cause of the condition or disorder.

For example, the methods of placing an SCU described herein are particularly useful for placing an SCU for maintaining or improving the functional capacity of an inactive limb or extremity. In such cases, the SCU can be used to stimulated paralyzed, weak, immobilized or underexercised muscle tissue without requiring voluntary exercise and for preventing various complications of prolonged physical confinement, including but not limited to pressure ulcers, deep venous thrombosis, autonomic dysreflexia and sensorimortor spasticity. The implanted SCU is employed in such cases to stimulate specific muscles in order to reduce the incidence and accelerate the healing of, for example, pressure ulcers on the sacrum, heels and other bony protuberances of bedridden or immobilized patients. Alternatively or additionally, the SCU is employed to reduce the possibility of venous stasis and embolus formation by eliciting regular muscle contractions in the legs of the bedridden or otherwise immobilized patient. Advantageously, in these cases, the SCU may be employed to produce a desired pattern of regular contractions in one or more muscles for periods of days or weeks without the need for ongoing, continuous patient or caregiver supervision.

The techniques described herein can also be applied in placing an SCU in a patient's head or neck for the treatment of various conditions and/or disorders such as headaches, facial pain, and/or epilepsy. However, it will be recognized that headaches, facial pain, and epilepsy are merely illustrative of the many different types of medical, psychiatric, and neurological conditions and disorders that exist and may be treated according to the principles described herein.

Epilepsy

Epilepsy is characterized by a tendency to recurrent seizures that can lead to loss of awareness, loss of consciousness, and/or disturbances of movement, autonomic function, sensation (including vision, hearing and taste), mood, and/or mental function. Epilepsy afflicts one to two percent of the population in the developed world. The mean prevalence of active epilepsy (i.e., continuing seizures or the need for treatment) in developed and undeveloped countries combined is estimated to be 7 per 1,000 of the general population, or approximately 40 million people worldwide. Studies in developed countries suggest an annual incidence of epilepsy of approximately 50 per 100,000 of the general population. However, studies in developing countries suggest this figure is nearly double at 100 per 100,000.

Epilepsy is often but not always the result of an underlying brain disease. Any type of brain disease can cause epilepsy, but not all patients with the same brain pathology will develop epilepsy. The cause of epilepsy cannot be determined in a number of patients; however, the most commonly accepted theory posits that it is the result of an imbalance of certain chemicals in the brain, e.g., neurotransmitters. Children and adolescents are more likely to have epilepsy of unknown or genetic origin. The older the patient, the more likely it is that the cause is an underlying brain disease such as a brain tumor or cerebrovascular disease.

Trauma and brain infection can cause epilepsy at any age, and in particular, account for the higher incidence rate in developing countries. For example, in Latin America, neurocysticercosis (cysts on the brain caused by tapeworm infection) is a common cause of epilepsy. In Africa, AIDS and its related infections, malaria and meningitis, are common causes. In India, AIDS, neurocysticercosis and tuberculosis, are common causes. Febrile illness of any kind, whether or not it involves the brain, can trigger seizures in vulnerable young children, which seizures are called febrile convulsions. About 5% of such children go on to develop epilepsy later in life. Furthermore, for any brain disease, only a proportion of sufferers will experience seizures as a symptom of that disease. It is therefore suspected that those who do experience such symptomatic seizures are more vulnerable for similar biochemical/neurotransmitter reasons.

Recent studies in both developed and developing countries have shown that up to 70 percent of newly diagnosed children and adults with epilepsy can be successfully treated (i.e., complete control of seizures for several years) with anti-epileptic drugs. After two to five years of successful treatment, drugs can be withdrawn in about 70 percent of children and 60 percent of adults without the patient experiencing relapses. However, up to 30 percent of patients are refractory to medication. There is evidence that the longer the history of epilepsy, the harder it is to control. The presence of an underlying brain disease typically results in a worse prognosis in terms of seizure control. Additionally, partial seizures, especially if associated with brain disease, are more difficult to control than generalized seizures.

Patients suffering from epilepsy may undergo surgery to remove a part of the brain in which the seizures are believed to arise, i.e., the seizure focus. However, in many patients a seizure focus cannot be identified, and in others the focus is in an area that cannot be removed without significant detrimental impact on the patient. For example, in temporal lobe epilepsy, patients may have a seizure focus in the hippocampi bilaterally. However, both hippocampi cannot be removed without adversely affecting a patient's long-term memory. Other patients may have a seizure focus that lies adjacent to a critical area such as the speech center.

Vagus nerve stimulation (VNS) has been applied with partial success in patients with refractory epilepsy. In this procedure, an implantable pulse generator (IPG) is implanted in the patient's thorax, and an electrode lead is routed from the IPG to the left vagus nerve in the neck. Based on a number of studies, approximately five percent of patients undergoing VNS are seizure-free, and an additional 30-40 percent of patients have a greater than 50 percent reduction in seizure frequency.

In addition to this relatively low efficacy, VNS may lead to significant side effects. The vagus nerve provides parasympathetic innervation to the cardiac tissue, and thus VNS may lead to bradycardia, arrhythmia, or even graver cardiac side effects. In fact, VNS systems may only be used on the left vagus nerve, as the right vagus nerve contributes significantly more to cardiac innervation. Additionally, VNS may interfere with proper opening of the vocal cords, which has led to hoarseness and shortness of breath in a significant number of VNS patients.

The exact mechanism of seizure suppression using VNS is unknown. The nucleus of tractus solitarius (NTS; a.k.a., nucleus of the solitary tract) is a primary site at which vagal afferents terminate. Because afferent vagal nerve stimulation has been demonstrated to have anticonvulsant effects, it is likely that changes in synaptic transmission in the NTS can regulate seizure susceptibility. To demonstrate this, Walker, et al. ("Regulation of limbic motor seizures by GABA and glutamate transmission in nucleus tractus solitarius," *Epilepsia*, August 1999) applied muscimol, an agonist of the inhibitory neurotransmitter GABA, to the NTS in a murine model of epilepsy. Muscimol applied to the NTS attenuated seizures in all seizure models tested, whereas muscimol applied to adjacent regions of NTS had no effect. Additionally, bicuculline methiodide, a GABA antagonist, injected into the NTS did not alter seizure responses. Finally, anticonvulsant effects were also obtained with application of lidocaine, a local anesthetic, into the NTS. Unilateral injections were sufficient to afford seizure protection. Walker, et al. conclude that inhibition of the NTS outputs enhances seizure resistance in the forebrain and provides a potential mechanism for the seizure protection obtained with vagal stimulation.

The NTS sends fibers bilaterally to the reticular formation and hypothalamus, which are important in the reflex control of cardiovascular, respiratory, and gastrointestinal functions. The NTS also provides input to the dorsal motor nucleus of the vagus, which enables the parasympathetic fibers of the vagus nerve to control these reflex responses. The NTS runs the entire length of the medulla oblongata, and the NTS (as well as the trigeminal nuclei) receives somatic sensory input from all cranial nerves, with much of its input coming from the vagus nerve.

Convincing evidence has been given that a significant number of neurons in the trigeminal nerve project to the NTS. By applying horseradish peroxidase to peripheral branches of the trigeminal nerve in a cat, it was found that branches of the trigeminal nerve (the lingual and pterygopalatine nerves) were found to contain fibers which ended ipsilaterally in the rostral portions of the NTS, massively in the medial and ventrolateral NTS, moderately in the intermediate and interstitial NTS, and sparsely in the ventral NTS. (The rostralmost part of the NTS was free from labeled terminals.) After injecting the enzyme into the NTS portions rostral to the area postrema, small neurons were scattered in the maxillary and mandibular divisions of the trigeminal ganglion. It was concluded that trigeminal primary afferent neurons project directly to the NTS. By staining for substance P immunoreactivity, it was found that Substance P containing trigeminal sensory neurons project to the NTS.

Convincing evidence has also been reported that a significant number of neurons in the trigeminal nuclei project to the NTS. Menetrey, et al used the retrograde transport of a protein-gold complex to examine the distribution of spinal cord and trigeminal nucleus caudalis neurons that project to the NTS in the rat. [See Menetrey, et al. "Spinal and trigeminal projections to the nucleus of the solitary tract: a possible substrate for somatovisceral and viscerovisceral reflex activation." *J Comp Neurol* 1987 January 15; 255(3):439-50.] The authors found that retrogradely labeled cells were numerous in the superficial laminae of the trigeminal nucleus caudalis, through its rostrocaudal extent. Since the NTS is an important relay for visceral afferents from both the glossopharyngeal and vagus nerves, the authors suggest that the spinal and trigeminal neurons that project to the NTS may be part of a larger system that integrates somatic and visceral afferent inputs from wide areas of the body. The projections may underlie somatovisceral and/or viscerovisceral reflexes, perhaps with a significant afferent nociceptive component.

Another study utilized microinfusion and retrograde transport of D [3H] aspartate to identify excitatory afferents to the NTS. The authors found that the heaviest labeling was localized bilaterally in the trigeminal nucleus with cells extending through its subdivisions and the entire rostrocaudal axis.

In addition, a study by Fanselow, et al. ("Reduction of pentylenetetrazole-induced seizure activity in awake rats by seizure-triggered trigeminal nerve stimulation," *Journal of Neuroscience*, November 2000) demonstrated that unilateral stimulation via a chronically implanted nerve cuff electrode applied to the infraorbital branch of the trigeminal nerve led to a reduction in electrographic seizure activity of up to 78 percent. The authors reported that bilateral trigeminal stimulation was even more effective.

The thalamus is believed to play a major role in some types of epilepsy by acting as a center for seizure onset or as a relay station in allowing a focal seizure to propagate. In a Single Positron Emission Computed Tomography (SPECT) study of patients with left-sided VNS systems, a consistent decrease of activity was found in the left thalamus caused by VNS. The authors concluded that left-sided VNS reduces seizure onset or propagation through inhibition of the thalamic relay center.

Thalamic relay neurons are essential in generating 3 Hz absence seizures and are believed to be involved in other types of epilepsy. Thalamic nuclei of some patients suffering from epilepsy display neuronal activities described as "low-threshold calcium spike bursts," which have been shown to be related to a state of membrane hyperpolarization of thalamic relay neurons. This thalamic rhythmicity is transmitted to the related cortex, thanks to thalamocortical resonant properties. In the cortex, an asymmetrical corticocortical inhibition (edge effect) at the junction between low and high frequency zones is proposed to be at the origin of a cortical activation of high frequency areas bordering low frequency ones.

Migraine Headache

The mechanism of a migraine is not well understood. Prevalent theories suggest that a migraine is a central nervous system neurovascular disorder and that the trigeminal or occipital nerves may play a prominent role. The trigeminal nerve carries virtually all of the sensation from the face, and thus it likely plays a role in any pain felt at the front or the top of the head.

In "Pathophysiology of migraine—new insights" (*Canadian Journal of Neurological Sciences*, November 1999), Hargreaves, et al. state that "the exact nature of the central dysfunction that is produced in migraines is still not clear and may involve spreading depression-like phenomena and activation of brainstem monoaminergic nuclei that are part of the central autonomic, vascular, and pain control centers. It is generally thought that local vasodilation of intracranial extracerebral blood vessels and a consequent stimulation of surrounding trigeminal sensory nervous pain pathways is a key mechanism underlying the generation of headache pain associated with migraine. This activation of the trigeminovascular system is thought to cause the release of vasoactive sensory neuropeptides, especially CGRP, that increase the pain response. The activated trigeminal nerves convey nociceptive information to central neurons in the brain stem trigeminal sensory nuclei that in turn relay the pain signals to higher centers where headache pain is perceived. It has been hypothesized that these central neurons may become sensitized as a migraine attack progresses." The disorder of migraine may ultimately evoke changes in blood vessels within pain-producing intracranial meningeal structures that give rise to headache pain.

Hargreaves, et al. further state that "the 'triptan' anti-migraine agents (e.g., sumatriptan, rizatriptan, zolmitriptan, and naratriptan) are serotonergic agonists that have been shown to act selectively by causing vasoconstriction through 5 HT1B receptors that are expressed in human intracranial arteries and by inhibiting nociceptive transmission through an action at 5-HT1D receptors on peripheral trigeminal sensory nerve terminals in the meninges and central terminals in brainstem sensory nuclei. These three complementary sites of action underlie the clinical effectiveness of the 5 HT1B/1D agonists against migraine headache pain and its associated symptoms."

In "Current concepts of migraine pathophysiology" (*Canadian Journal of Neurological Sciences*, Autumn 1999), Hamel cites evidence that indicates migraine originates in the brain and, in its process and evolution, affects the meningeal blood vessels and leads to the development of head pain. Hamel states that "this manifestation is related to the activation of the trigeminovascular sensory nerves, which release neuropeptides that mediate vasodilation, and the proinflammatory reaction thought to be involved in pain generation and transmission. Such a concept underscores the fact that the relationship between the nerves and the blood vessels is of paramount importance in the manifestation of the disease's symptoms."

It has also been suggested that primary headache syndromes, such as cluster headache and migraine, share an anatomical and physiologic substrate, namely the neural innervation of the cranial circulation. In "The Trigeminovascular System in Humans: Pathophysiologic Implications for Primary Headache Syndromes of the Neural Influences on the Cerebral Circulation" (*Journal of Cerebral Blood Flow Metabolism*, February 1999), May, et al. report that observations of vasodilation were made in an experimental trigeminal pain study. They conclude that the observed dilation of these vessels in trigeminal pain is not inherent to a specific headache syndrome, but rather is a feature of the trigeminal neural innervation of the cranial circulation. They also state that clinical and animal data suggest that the observed vasodilation is, in part, an effect of a trigeminoparasympathetic reflex. They suggest that the trigeminal innervation of the cranial circulation and the observed vasodilation of the associated vasculature during headache syndromes may be an underlying pathophysiological mechanism of headache.

In "Intraoral Chilling versus Oral Sumatriptan for Acute Migraine" (*Heart Disease*, November-December 2001), Friedman, et al. state that "recent evidence suggests that the primary inflammation occurs in the maxillary nerve segment [of the trigeminal nerve], accessible intraorally. Local tenderness, related to symptom laterality, has been palpated in asymptomatic migraine patients."

In "Cluster Headache" (*Current Treatment Options in Neurology*, November 1999), Salvesen suggests a possible link between the trigeminal nerve and cluster headache: "for a very limited group of patients with chronic cluster headache, surgery may be a last resort. The best surgical options are probably radio-frequency rhizotomy or microvascular decompression of the trigeminal nerve." In a recent study involving eighteen patients, fifteen patients obtained immediate pain relief from chronic intractable cluster headaches after one or two injections of percutaneous retrogasserian glycerol rhizolysis. However, cluster headache recurred in seven patients over the course of the study, suggesting that permanent trigeminal destruction may not be an effective treatment.

For many years, Transcutaneous Electrical Nerve Stimulation (TENS) has been applied with some success to the control of headache and facial pain symptoms. TENS is used to modulate the stimulus transmissions by which pain is felt by applying low-voltage electrical stimulation to large peripheral nerve fibers via electrodes placed on the skin. A study of 282 migraineurs had patients undergo Punctual (i.e., episodic) Transcutaneous Electrical Nerve Stimulation (PuTENS) via pocket electrostimulators. After more than 6 months PuTENS was prophylactically effective in eighty percent of the patients in the study, i.e., their frequency of attacks and use of drugs were reduced by at least fifty percent. However, TENS devices can produce significant discomfort and can only be used intermittently.

TABLE 1

Groupings of Headache Disorders and Facial Pain
The International Headache Society (IHS) published "Classification and Diagnostic Criteria for Headache Disorders, Cranial Neuralgias and Facial Pain" in 1988. IHS identified 13 different general groupings of headache, givin below in Table 1.

| | |
|---|---|
| 1) | Migraine |
| 2) | Tension-type headache |
| 3) | Cluster headache and chronic paroxysmal hemicrania |
| 4) | Miscellaneous headaches unassociated with structural lesions |
| 5) | Headache associated with head trauma |
| 6) | Headache associated with vascular disorders |
| 7) | Headache associated with non-vascular intracranial disorder |
| 8) | Headache associated with substances or their withdrawal |
| 9) | Headache associated with non-cephalic infections |
| 10) | Headaches associated with metabolic disorders |
| 11) | Headache or facial pain associated with disorder of cranium, neck, eyes, ears, nose, sinuses, teeth, mouth or other facial or cranial structures |
| 12) | Cranial neuralgias, nerve trunk pain and deafferentation pain |
| 13) | Non-classifiable headache |

The IHS classification of the most common types of headache is summarized in Table 2 below.

TABLE 2

IHS Classification of Primary Headaches

1. Migraine
1.1 Migraine without aura
1.2 Migraine with aura
1.2.1 Migraine with typical aura
1.2.2 Migraine with prolonged aura
1.2.3 Familial hemiplegic migraine headache
1.2.4 Basilar migraine
1.2.5 Migraine aura without headache
1.2.6 Migraine with acute onset aura
1.3 Ophthalmoplegic migraine
1.4 Retinal migraine
1.5 Childhood periodic syndromes that may be precursors to or associated with migraine
1.5.1 Benign paroxysmal vertigo of childhood
1.5.2 Alternating hemiplegia of childhood
1.6 Complications of migraine
1.6.1 Status migrainosus
1.6.2 Migrainous infarction
1.7 Migrainous disorder not fulfilling above criteria
2. Tension-type headache
2.1 Episodic tension-type headache

TABLE 2-continued

IHS Classification of Primary Headaches 2.1.1 Episodic tension-type headache associated with disorder of pericranial muscles
2.1.2 Episodic tension-type headache not associated with disorder of pericranial muscles
2.2 Chronic tension-type headache
2.2.1 Chronic tension-type headache associated with disorder of pericranial muscles
2.2.2 Chronic tension-type headache not associated with disorder of pericranial muscles
2.3 Headache of the tension-type not fulfilling above criteria
3. Cluster headache and chronic paroxysmal hemicrania
3.1 Cluster Headache
3.1.1 Cluster headache, periodicity undetermined
3.1.2 Episodic cluster headache
3.1.3. Chronic Cluster Headache
3.1.3.1 Unremitting from onset
3.1.3.2 Evolved from episodic
3.2 Chronic paroxysmal hemicrania
3.3 Cluster headache-like disorder not fulfilling above Criteria

TABLE 3

IHS Diagnostic Criteria for Migraine Without Aura
The IHS classification provides diagnostic criteria for migraine without and with aura, summarized in Tables 3 and 4 below.

A. At least five attacks fulfilling B–D below:
B. Headache attacks lasting 4–72 hours (untreated or unsuccessfully treated)
C. Headache has at least two of the following characteristics:
   1. Unilateral location
   2. Pulsating quality
   3. Moderate or severe intensity (inhibits or prohibits daily activities)
   4. Aggravation by walking stairs or similar routine physical activity
D. During headache at least one of the following:
   1. Nausea and/or vomiting
   2. Photophobia and phonophobia
E. At least one of the following:
   1. History and physical do not suggest headaches secondary to organic or systemic metabolic disease
   2. History and/or physical and/or neurologic examinations do suggest such disorder, but is ruled out by appropriate investigations
   3. Such disorder is present, but migraine attacks do not occur for the first time in close temporal relation to the disorder

TABLE 4

IHS Diagnostic Criteria for Migraine With Aura

A. At least two attacks fulfilling B below:
B. At least three of the following four characteristics:
   1. One or more fully reversible aura symptoms indicating focal cerebral cortical and/or brain stem dysfunction
   2. At least one aura symptom develops gradually over more than four minutes or two or more symptoms occur in succession
   3. No aura symptom lasts more than 60 minutes. If more than one aura symptom is present, accepted duration is proportionally increased
   4. Headache follows aura with a free interval of less than 60 minutes. It may also begin before or simultaneously with the aura.
C. At least one of the following:
   1. History and physical and neurologic examinations do not suggest headaches secondary to organic or systemic metabolic disease
   2. History and/or physical and/or neurologic examinations do suggest such disorder, but it is ruled out by appropriate investigations
   3. Such disorder is present, but migraine attacks do not occur for the first time in close temporal relation to the disorder The IHS classification includes several different types of migraine variants. Basilar migraine is defined as a migraine with an aura involving the brainstem. Symptoms include ataxia, dysarthria, vertigo, tinnitus and/or changes in consciousness and cognition. Ophthalmoplegic migraine is associated with acute attacks of third nerve palsy with accompanying dilation of the pupil. In this setting, the differential diagnosis includes an intracranial aneurysm or chronic sinusitis complicated by a mucocele. The ophthalmoplegia can last from hours to months. Hemiplegic migraine is distinguished by the accompanying hemiplegia, which can be part of the aura, or the headache may precede the onset of hemiplegia. Hemiplegic migraine can be familial and may last for days or weeks, clinically simulating a stroke. An additional differential diagnosis includes focal seizures.

Status migrainosus describes a migraine lasting longer than 72 hours with intractable debilitating pain, and typically occurs in a setting of inappropriate and prolonged use of abortive anti-migraine drugs. These patients may require hospitalization, both for pain control, detoxification from the abused drugs, and treatment of dehydration resulting from prolonged nausea and vomiting.

A migraine prevalence survey of American households was conducted in 1992, and included 20,468 respondents 12-80 years of age. Using a self-administered questionnaire based on modified IHS criteria, 17.6% of females and 5.7% of males were found to have one or more migraine headaches per year. A projection to the total US population suggests that 8.7 million females and 2.6 million males suffer from migraine headache with moderate to severe disability. Of these, 3.4 million females and 1.1 million males experience one or more attacks per month. Prevalence is highest between the ages of 25 and 55, during the peak productive years.

Based on published data, the Baltimore County Migraine Study, MEDSTAT's MarketScan medical claims data set, and statistics from the Census Bureau and the Bureau of Labor Statistics, it has been estimated that migraineurs require 3.8 bed rest days for men and 5.6 days for women each year, resulting in a total of 112 million bedridden days. Migraine costs American employers about $13 billion a year because of missed workdays and impaired work function—close to $8 billion is directly due to missed workdays. Patients of both sexes aged 30 to 49 years incurred higher indirect costs compared with younger or older employed patients. Annual direct medical costs for migraine care are about $1 billion, with about $100 spent per diagnosed patient. Physician office visits account for about 60% of all costs; in contrast, emergency department visits contribute less than 1% of the direct costs.

Tension-Type Headache

The diagnostic criteria for tension-type headaches are summarized in Table 5 below. However, migraine symptoms may overlap considerably with those of tension-type headaches. Tension-type headaches are believed by some experts to be a mild variant of migraine headache. Patients with tension-type headaches who also have migraines may experience nausea and vomiting with a tension headache, though when they do, it typically is mild and for a shorter duration compared to that with a migraine. Tension-type headache may be a disorder unto itself in individuals who do not have migraines, and may manifest as attacks of mild migraine in individuals with migraines.

TABLE 5

IHS Criteria for Various Forms of Tension-Type Headache

Tension-type headache

At least two of the following pain characteristics:

1. Pressing/tightening (non-pulsating) quality
2. Mild or moderate intensity (may inhibit, but does not prohibit activities)
3. Bilateral location
4. No aggravation by walking stairs or similar routine physical activity Both of the following:

1. No nausea or vomiting (anorexia may occur)
2. Photophobia and phonophobia absent, or only one is present At least one of the following:

1. History and physical do not suggest headaches secondary to organic or systemic metabolic disease
2. History and/or physical and/or neurologic examinations do suggest such disorder, but is ruled out by appropriate investigations
3. Such disorder is present, but tension-type headache does not occur for the first time in close temporal relation to the disorder Episodic tension-type headache (ETTH)

Diagnostic criteria:

A. At least 10 previous episodes, <180 days/year (<15/mo) with headache
B. Headache lasting from 30 minutes to 7 days Chronic tension-type headache (CTTH)

Diagnostic criteria:

A. Average frequency ≧1 day/month (≧189 days/year) for ≧6 months

Tension-type headache associated with disorder of pericranial muscles

At least one of the following:

1. Increased tenderness of pericranial muscles demonstrated by manual palpation or pressure algometer.
2. Increased electromyographic level of pericranial muscles at rest or during physiologic tests.

Tension-type headache not associated with pericranial muscle disorder

No increased tenderness of pericranial muscles. If studied, electromyography of pericranial muscles shows normal levels of activity.

Based on a telephone survey of 13,345 people, the 1-year period prevalence of episodic tension-type headache (ETTH) is estimated to be 38.3%, according to IHS criteria. Women had a higher 1-year ETTH prevalence than men in all age, race, and education groups, with an overall prevalence ratio of 1.16. Prevalence peaked in the 30- to 39-year-old age group in both men (42.3%) and women (46.9%). Prevalence increased with increasing educational levels in both sexes, reaching a peak in subjects with graduate school educations of 48.5% for men and 48.9% for women. Of subjects with ETTH, 8.3% reported lost workdays because of their headaches, while 43.6% reported decreased effectiveness at work, home, or school.

Chronic Daily Headache

Chronic tension-type headache (CTTH) is a subtype of tension headaches, with patients experiencing headaches daily or almost every day. In practice, the term "chronic daily headache" is commonly used to describe headaches lasting for greater than 4 hours per day and for at least 15 days per month. The classification of chronic daily headaches is summarized below in Table 6.

TABLE 6

Classification of Chronic Daily Headache

Transformed migraine
1. With medication overuse
2. Without medication overuse

Chronic tension-type headache (CTTH)
1. With medication overuse
2. Without medication overuse New daily persistent headache
1. With medication overuse
2. Without medication overuse Hemicrania continua
1. With medication overuse
2. Without medication overuse In the study of 13,345 people cited above, the 1-year period prevalence of chronic tension-type headache (CTTH) was estimated to be 2.2%. This prevalence was higher in women and declined with increasing education. Subjects with CTTH reported more lost workdays (mean of 27.4 days vs. 8.9 days for those reporting lost workdays) and reduced-effectiveness days (mean of 20.4 vs. 5.0 days for those reporting reduced effectiveness) compared with subjects with ETTH.

Chronic daily headaches are best conceptualized as an umbrella category term referring to a group of headache disorders characterized by headaches which occur greater than 15 days per month, with an average untreated duration of greater than 4 hours per day. There are many secondary causes of chronic daily headache, including post-traumatic headache, arthritis, intracranial mass lesions, etc. There are also short-lived primary headache disorders that occur greater than 15 days per month, such as chronic cluster headache or the paroxysmal hemicranias. The most common primary, chronic daily headache disorders include transformed migraine, chronic tension-type headaches, new daily persistent headache, or hemicrania continua. Each of these diagnoses can be complicated by medication overuse (e.g., barbiturates, acetaminophen, aspirin, caffeine, ergotamine tartrate and opioids). When used daily, all of these medications can lead to a vicious cycle of rebound headaches.

Cluster Headache

The 1988 IHS classification system recognized the uniqueness of cluster headache as a clinical and epidemiological entity. Formerly classified as a vascular migraine variant, cluster headache (a.k.a. suicide headache) is thought to be one of the most severe headache syndromes. It is characterized by attacks of severe pain, generally unilateral and orbital and lasting 15 minutes to 3 hours, with one or more symptoms such as unilateral rhinorrhea, nasal congestion, lacrimation, and conjunctival injection. In most patients, headaches occur in episodes, generally with a regular time pattern. These "cluster periods" last for weeks to months, separated by periods of remission lasting months to years. These headaches primarily affect men and in many cases patients having distinguishing facial, body, and psychological features. Several factors may precipitate cluster headaches, including histamine, nitroglycerin, alcohol, transition from rapid eye movement (REM) to non-REM sleep, circadian periodicity, environmental alterations, and change in the level of physical, emotional, or mental activity. The IHS classification system gives specific diagnostic criteria for cluster headache, as given in Table 7 below.

TABLE 7

IHS Diagnostic Criteria for Cluster Headache 3.1 Cluster Headache
A. At least 5 attacks fulfilling B-D below:
B. Severe unilateral, orbital, supraorbital and/or temporal pain lasting 15–180 minutes untreated
C. At least one of the following signs present on the pain side:
   1. Conjunctival injection
   2. Lacrimation
   3. Nasal congestion
   4. Rhinorrhea
   5. Forehead and facial sweating
   6. Miosis
   7. Ptosis
   8. Eyelid edema
D. Frequency of attacks: from 1 every other day to 8 per day
E. At least one of the following:
   1. History, physical and neurological examinations do not suggest one of the disorders listed in groups 5–11 of Table 1
   2. History and/or physical and/or neurological examinations do suggest such disorder, but it is ruled out by appropriate investigations
   3. Such disorder is present, but cluster headache does not occur for the first time in close temporal relation to the disorder
3.1.1 Cluster headache periodicity undefined
   A. Criteria for 3.1 fulfilled
   B. Too early to classify as 3.1.2 or 3.1.3
3.1.2 Episodic cluster headache
Description: Attacks lasting between 1 week and 3 months occur in periods lasting 1 week to one year separated by pain free periods lasting 14 days or more.
   A. All the letter headings of 3.1
   B. At least 2 periods of headaches (cluster periods) lasting (untreated) from 7 days to one year, separated by remissions of at least 14 days.
3.1.3 Chronic cluster headache
Description: Attacks lasting between 2 weeks and 3 months occur for more than one year without remission or with remissions lasting less than 14 days.
   A. All the letter headings of 3.1

TABLE 7-continued

IHS Diagnostic Criteria for Cluster Headache

B. Absence of remission phases for one year or more or with remissions lasting less than 14 days.
3.1.3.1 Chronic cluster headache unremitting from onset
 A. All the letter headings of 3.1.3
 B. Absence of remission periods lasting 14 days or more from onset.
3.1.3.2 Chronic cluster headache evolved from episodic
 A. All the letter headings of 3.1.3
 B. At least one interim remission period lasting 14 days or more within one year after onset, followed by unremitting course for at least one year.

The estimated prevalence of cluster headache is 69 cases per 100,000 people. Men are affected more commonly than women in a proportion of 6:1. Although most patients begin experiencing headache between the ages of 20 and 50 years (mean of 30 years), the syndrome may begin as early as the first decade and as late as the eighth decade.

Cervicogenic Headache

Cervicogenic headache (CEH) is a headache with its origin in the neck area. The source of pain is in structures around the neck that have been damaged. These structures can include joints, ligaments, muscles, and cervical discs, all of which have complex nerve endings. When these structures are damaged, the nerve endings send pain signals up the pathway from the upper nerves of the neck to the brainstem. These nerve fibers may synapse in the same brainstem nuclei as the nerve fibers of the trigeminal nerve. Since the trigeminal nerve is responsible for the perception of head pain, the patient experiences the symptoms of headache and/or facial pain.

While many patients who are diagnosed with CEH have the traditional symptoms of tension-type headache, some of the patients who have the traditional symptoms of migraine and cluster headache also respond to CEH diagnosis and treatment.

Facial Pain

Facial pain may be due to a number of underlying disorders. Among the most common is Trigeminal Neuralgia (also known as tic douloureux). More than 50,000 people in the United States suffer from trigeminal neuralgia. This disorder may cause episodes of intense, stabbing, electric shock-like pain in the areas of the face where the branches of the nerve are distributed (e.g., the lips, eyes, nose, scalp, forehead, upper jaw, and lower jaw). A less common form of the disorder, Atypical Trigeminal Neuralgia, may cause less intense, constant, dull burning or aching pain, sometimes with occasional electric shock-like stabs. Both forms of the disorder most often affect one side of the face, but some patients experience pain at different times on both sides. Onset of symptoms occurs most often after age 50, and it affects women more often than men. For patients with this disorder, an ordinary touch of the face, such as when brushing teeth or applying makeup, can trigger an attack. Trigeminal neuralgia is believed to be due to hyper-excitability of fibers of the trigeminal nerve or its ganglion. Microelectrode recordings from the trigeminal ganglion have demonstrated sustained high-frequency bursts during pain episodes of trigeminal neuralgia.

Trigeminal neuralgia may be treated medically with drugs that decrease neural excitability, e.g., carbamazepine or phenytoin. However, such medications prove ineffective for many patients over the course of the disease. Thus, a number of surgical interventions (e.g., microvascular decompression of the trigeminal ganglion or it nerve fibers, radio-frequency rhizotomy) have been developed.

Another cause of facial pain is Temporomandibular Joint (TMJ) Dysfunction Syndrome. Most TMJ discomfort is temporary and can be treated with inexpensive remedies. However, some TMJ dysfunction patients are afflicted with persistent and sometimes unbearable pain. The symptoms of this chronic dysfunction include persistent pain in the facial muscles on one or both sides, a clicking or popping sensation when opening the mouth or working the jaw, recurring headaches, and difficulty chewing. Analgesics and anti-inflammatory medication may relieve the pain in some patients. Others turn to TMJ surgery in desperation.

Yet another cause of facial pain is Postherpetic Neuralgia, which is a possible complication of herpes zoster reactivation ("shingles"). The herpes zoster virus may cause chicken pox upon initial infection. When reactivated, the virus causes shingles—a painful disease characterized by eruptions along a nerve path often accompanied by severe neuralgia and a skin rash. It can affect the torso or limbs (spinal ganglia shingles) or the face (trigeminal ganglia shingles). Approximately one in five adults develops shingles, usually after age 50. For most people, shingles is an acute condition with pain typically lasting one month. However, in older patients or patients with a compromised immune system, singles can lead to postherpetic neuralgia, a very painful chronic condition in which the pain associated with the shingles persists beyond one month, even after the rash is gone. The incidence of postherpetic neuralgia is almost negligible before age 50, but at least 50% of patients older than 60 years and almost 75% beyond age 70 become affected following a shingles attack. Postherpetic neuralgia tends to improve over time without treatment. Some estimates suggest that only two to three percent of patients have pain lasting more than one year. However, since more than 60,000 new cases develop annually in the US, the collective morbidity is still substantial. Treatment of postherpetic neuralgia consists of symptomatic relief of severe pain with tricyclic antidepressants and opioids.

Other Medical, Psychiatric, and Neurological Conditions and Disorders

Other medical, psychiatric, and neurological conditions and/or disorders include, but are not limited to, the following:

1) Pain resulting from one or more medical conditions including, but not limited to: migraine headaches, including but not limited to migraine headaches with aura, migraine headaches without aura, menstrual migraines, migraine variants, atypical migraines, complicated migraines, hemiplegic migraines, transformed migraines, and chronic daily migraines; episodic tension headaches; chronic tension headaches; analgesic rebound headaches; episodic cluster headaches; chronic cluster headaches; cluster variants; chronic paroxysmal hemicrania; hemicrania continua; post-traumatic headache; post-traumatic neck pain; post-herpetic neuralgia involving the head or face; pain from spine fracture secondary to osteoporosis; arthritis pain in the spine, headache related to cerebrovascular disease and stroke; headache due to vascular disorder; musculoskeletal neck pain; reflex sympathetic dystrophy, cervicalgia; glossodynia, carotidynia; cricoidynia; otalgia due to middle ear lesion; gastric pain; sciatica; maxillary neuralgia; laryngeal pain, myalgia of neck muscles; trigeminal neuralgia; post-lumbar puncture headache; low cerebro-spinal fluid pressure headache; temporomandibular joint disorder; atypical facial pain; ciliary neuralgia; paratrigeminal neuralgia; petrosal neuralgia; Eagle's syndrome; idiopathic intracranial hypertension; orofacial pain; myofascial pain syndrome involving the head, neck, and shoulder; chronic migraneous neuralgia, cervical headache; paratrigeminal paralysis; sphenopalatine ganglion neuralgia; carotidynia; Vidian neuralgia; and causalgia.

2) Epilepsy, including, but not limited to, generalized and partial seizure disorders.

3) Cerebrovascular diseases resulting from one or more medical conditions including, but not limited to, atherosclerosis, aneurysms, strokes, and cerebral hemorrhage.

4) Autoimmune diseases resulting from one or more medical conditions including, but not limited to, multiple sclerosis.

5) Sleep disorders resulting from one or more medical conditions including, but not limited to, sleep apnea and parasomnias.

6) Autonomic disorders resulting from one or more medical conditions including, but not limited to: gastrointestinal disorders, including, but not limited to, gastrointestinal motility disorders, nausea, vomiting, diarrhea, chronic hiccups, gastroesphageal reflux disease, and hypersecretion of gastric acid; autonomic insufficiency; excessive epiphoresis; excessive rhinorrhea; and cardiovascular disorders including, but not limited to, cardiac dysrythmias and arrythmias, hypertension, and carotid sinus disease.

7) Urinary bladder disorders resulting from one or more medical conditions including, but not limited to, spastic and flaccid bladder.

8) Abnormal metabolic states resulting from one or more medical conditions including, but not limited to, hyperthyroidism and hypothyroidism.

9) Disorders of the muscular system resulting from one or more medical conditions including, but not limited to, muscular dystrophy and spasms of the upper respiratory tract and face.

10) Neuropsychiatric disorders resulting from one or more medical conditions including, but not limited to, depression, schizophrenia, bipolar disorder, autism, personality disorders, and obsessive-compulsive disorder.

For ease of explanation, the term "medical condition" will be used herein and in the appended claims, unless otherwise specifically denoted, to refer to any medical, psychiatric, and/or neurological condition and/or disorder described herein, listed above, or related or similar to any condition or disorder described or listed herein.

FIGS. 9 and 10 depict the upper cervical spine (C1-C4) area of a patient. As shown in FIGS. 9 and 10, a number of nerves arise from the upper cervical spine (C1-C4). Examples of such nerves include, but are not limited to, the greater occipital nerve(s) (130), the lesser occipital nerve(s) (132), the third occipital nerve(s) (134), greater auricular nerve(s) (136), transverse cervical nerve(s) (138), the supraclavicular nerve(s) (139), and/or branches of any of these nerves. As shown in FIG. 10, the occipital nerves (130, 132, 134) are relatively easily accessed, especially in their distal portions, since they lie subcutaneously in the back of the head and upper neck.

In some embodiments, at least one stimulus is applied with a system control unit (SCU) to one or more target nerves of a patient to treat and/or prevent one or more of the medical conditions listed above. The target nerve may be any nerve originating in the upper cervical spine area (i.e., C1-C4) or any branch of a nerve originating in the upper cervical spine area. For example, the target nerve may include, but is not limited to, the greater occipital nerve(s) (130), the lesser occipital nerve(s) (132), the third occipital nerve(s) (134), greater auricular nerve(s) (136), transverse cervical nerve(s) (138), the supraclavicular nerve(s) (139), and/or branches of any of these nerves. The greater (130), lesser (132), and third occipital nerves (134), as well as the greater auricular nerves (136), are relatively easily accessed, especially in their distal portions, since they lie subcutaneously in the back of the head and upper neck. An SCU may thus be easily implanted via injection and/or via endoscopic means adjacent to one or more of these nerves and then optimally positioned using the systems and methods described herein. A more complicated surgical procedure may be required for sufficient access to one or more of these nerves and/or for purposes of fixing the SCU in place. The sites of injection or skin incision may be selected such that the resulting scars would likely be covered by hair on most people.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A system comprising:
   an implantable system control unit (SCU) configured to provide a stimulus to a patient;
   two lines attached to said SCU at two respective attachment points for pulling said SCU in different directions into position during placement of said SCU within said patient; and
   two caps respectively disposed over said two attachment points.

2. The system of claim 1, further comprising a plurality of electrodes configured to deliver an electrical stimulation to said patient.

3. The system of claim 1, wherein each of said two lines comprises suture silk.

4. The system of claim 1, further comprising two eyelets on said SCU to which said two lines are respectively attached.

5. The system of claim 1, wherein said electrodes are mounted to the SCU.

6. The system of claim 1, wherein said first line and said second line are respectively attached to opposite ends of said SCU, such that said SCU can be pulled in opposite directions.

7. A method of positioning an implantable system control unit (SCU) within a patient comprising:
   threading a first line through said patient using a needle, such that said first line passes proximal to target tissue that is to be stimulated by said SCU; and
   pulling said SCU in different directions into place with said first line attached to said SCU and a second line attached to said SCU, such that said SCU is proximal to said target tissue.

8. The method of claim 7, further comprising applying an electrical stimulation pulse to said needle when inserting said needle proximal to said target tissue to confirm that said needle is passing proximal to said target tissue.

9. The method of claim 8, further comprising repositioning said needle based on effects of said electrical stimulation pulse.

10. The method of claim 7, further comprising flossing said SCU into position by pulling selectively on both said first line and said second line.

11. The method of claim 7, further comprising securing said SCU in position.

12. The method of claim 11, wherein securing said SCU is performed by securing said second line at a needle insertion point and securing said first line at a needle exit point.

13. The method of claim 12, wherein securing said first line and said second line comprises suturing said second line at said needle insertion point and suturing said first line at said needle exit point.

14. The method of claim 7, wherein said target tissue is located in a neck of said patient and said threading said first line comprises threading said first line through a portion of said patient's neck.

15. The method of claim 7, wherein said target tissue is located in a limb of said patient and said threading said first line comprises threading said first line through a portion of said patient's limb.

16. The method of claim 7, further comprising threading said first line through an anchor point to curve a path of implantation.

17. The method of claim 16, further comprising creating said anchor point by inserting a tool within said patient along which said first line is guided when pulling said SCU.

18. The method of claim 7, wherein the SCU is pulled in opposite directions.

19. The method of claim 7, wherein said SCU is pulled in different directions while said second line extends from a needle insertion point and while said first line extends from a needle exit point.

20. The method of claim 7, further comprising attaching said first line to said SCU after said first line has been threaded through said patient.

21. The method of claim 7, wherein said needle is curved, such that said first line is threaded along a curved path.

22. A system comprising:
an implantable system control unit (SCU) configured to provide a stimulus to a patient;
a member attached to said SCU at an attachment point for pulling said SCU into position within said patient; and
a cap disposed over said attachment point.

23. The system of claim 22, further comprising a plurality of electrodes configured to deliver an electrical stimulation to said patient.

24. The system of claim 22, wherein said member comprises a line.

25. The system of claim 24, wherein said line comprises suture silk.

26. The system of claim 24, further comprising two lines attached to said SCU for pulling said SCU in different directions during placement of said SCU within said patient.

27. The system of claim 24, further comprising an eyelet on said SCU to which said line is attached.

* * * * *